US008945932B2

(12) United States Patent
Patton et al.

(10) Patent No.: US 8,945,932 B2
(45) Date of Patent: Feb. 3, 2015

(54) METHODS AND COMPOSITIONS FOR DETECTING AND ISOLATING PHOSPHORYLATED MOLECULES USING HYDRATED METAL OXIDES

(75) Inventors: Wayne F. Patton, Newton, MA (US); Alvydas Mikulskis, West Roxbury, MA (US); Eva Golenko, Waltham, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 1289 days.

(21) Appl. No.: 11/571,687

(22) PCT Filed: Jul. 6, 2005

(86) PCT No.: PCT/US2005/023810
§ 371 (c)(1),
(2), (4) Date: May 19, 2008

(87) PCT Pub. No.: WO2006/014424
PCT Pub. Date: Feb. 9, 2006

(65) Prior Publication Data
US 2008/0261321 A1    Oct. 23, 2008

Related U.S. Application Data

(60) Provisional application No. 60/521,804, filed on Jul. 6, 2004, provisional application No. 60/644,181, filed on Jan. 14, 2005.

(51) Int. Cl.
*G01N 33/52* (2006.01)
*C12Q 1/68* (2006.01)
*C07K 1/22* (2006.01)
*G01N 33/68* (2006.01)

(52) U.S. Cl.
CPC .............. *C12Q 1/6818* (2013.01); *C07K 1/22* (2013.01); *G01N 33/6842* (2013.01)
USPC .............. 436/86; 436/174; 436/177; 436/178

(58) Field of Classification Search
CPC ..... C07K 1/22; C12Q 1/6818; G01N 33/6842
USPC .............. 436/86, 73, 83, 103, 104, 164, 166, 436/172, 174, 177, 178; 250/304; 356/38
See application file for complete search history.

(56) References Cited

U.S. PATENT DOCUMENTS

| 5,395,498 A * | 3/1995 | Gombinsky et al. .......... 204/464 |
| 6,652,875 B1 | 11/2003 | Bannister |
| 2005/0017525 A1 | 1/2005 | Douziech |
| 2006/0014234 A1 | 1/2006 | Tepe |

FOREIGN PATENT DOCUMENTS

| JP | 2003-179269 | 1/2004 |
| JP | 2004-509638 | 4/2004 |
| JP | 2005-017013 | 1/2005 |
| WO | 02/27318 A | 4/2002 |
| WO | WO 02/27318 | 4/2002 |
| WO | WO 03/065031 | 8/2003 |
| WO | 2004/104590 A | 12/2004 |

OTHER PUBLICATIONS

Clapp, Aaron R. et al. "Fluorescence resonance energy transfer between quantum dot donors and dye-labeled protein acceptors." Journal of the American Chemical Society (online Dec. 2003) 126 301-310.*
Hampl, Johannes et al. "Upconverting phosphor reporters in immunochromatographic assays." Analytical Biochemistry (2001) 288 176-187.*
Nelson, Jennifer A. et al. "Nanocrystalline Y_2 O_3:Eu phosphors prepared by alkalide reduction." Chemistry of Materials (2003) 15 688-693.*
Zhang, Chao, et al. "Application of the biological conjugate between antibody and colloid Au nanoparticles as analyte to inductively coupled plasma mass spectrometry." Analytical Chemistry (2002) 74 96-99.*
Healy, Kevin E. et al. "Hydration and preferential molecular adsorption on titanium in vitro." Biomaterials (1992) 13 553-561.*
Guerrero, G. et al. "Anchoring of phosphonate and phosphinate coupling molecules on titania particles." Chemistry of Materials (2001) 13 4367-4373.*
Peng, Z. G. et al. "Adsorption of bovine serum albumin on nanosized magnetic particles." Journal of Colloid and Interface Science (2004) 271 277-283.*
Beydoun, Donia et al. "Novel photocatalyst: titania-coated magnetite. Activity and photodissolution." J Phys Chem B (2000) 104 4387-4396.*
Markin, Chad et al. "A DNA-based method for rationally assembling nanoparticles into macroscopic materials." Nature (1996) 382 607-609.*
Coletti-Previero et al., Alumina-Phosphate Complexes for Immobilization of Biomolecules, Anal Biochem. 180:1-10 (1989).

(Continued)

*Primary Examiner* — Christopher A Hixson
(74) *Attorney, Agent, or Firm* — Fish & Richardson P.C.

(57) ABSTRACT

The invention provides methods for detecting and isolating phosphomolecules using phosphoaffinity materials that comprise a hydrated metal oxide. In an embodiment, a method for detecting a phosphomolecule in a sample involves (a) contacting a sample with a phosphoaffinity material comprising a hydrated metal oxide, under conditions wherein a phosphomolecule is capable of binding to the phosphoaffinity material to form a phosphomolecule-phosphoaffinity material complex, and (b) detecting formation of a phosphomolecule-phosphoaffinity material complex, thereby detecting a phosphomolecule in the sample. In another embodiment, a method for isolating a phosphomolecule from a sample involves (a) contacting a sample with a phosphoaffinity material comprising a hydrated metal oxide, under conditions wherein a phosphomolecule is capable of binding to the phosphoaffinity material to form a phosphomolecule-phosphoaffinity material complex, wherein the hydrated metal oxide comprises yttrium, and (b) separating the phosphomolecule-phosphoaffinity material complex from the sample, thereby isolating the phosphomolecule from the sample.

33 Claims, 17 Drawing Sheets

(56) References Cited

OTHER PUBLICATIONS

Damen, et al., Induction of Calcium Phosphate Precipitation by Titanium Dioxide, J. Dent Res 70(10):1346-9 (Oct. 1991); Erratum in: J Dent Res 71(1):78 (Jan. 1992).
Debruyne, Staining of Alkali-Labile Phosphoproteins and Alkaline Phosphatases on Polyacrylamide Gels, Anal Biochem. 133(1):110-5 (Aug. 1983).
Ficarro et al., Phosphoproteome Analysis by Mass Spectrometry and Its Application to *Saccharomyces cerevisiae*, Nat Biotechnol 20(3):301-5 (Mar. 2002).
Grosman et al., Aluminum Acid Alizarin Violet: a General Purpose Nuclear Fluorochrome, Biotech Histochem 72(6):299-303 (Nov. 1997).
Ikeguchi et al., Determination of Organic Phosphates by Column-Switching High Performance Anion-Exchange Chromatography Using On-Line Preconcentration of Titania, Anal Sci 13(3):479-483 (Jun. 1997).
Ishikawa et al., Simultaneous Determination of Eleven Dyes and Their Aluminum Lakes in Drugs, J AOAC Int. 86(2):215-21 (Mar.-Apr. 2003).
Kim et al., A Study on the Adsorption Characteristics of Orthophosphates on Rutile-Type Titanium Dioxide in Aqueous Solutions, J Colloid Interface Sci 1:233(1):31-37 (Jan. 2001).
Koppel et al., Affinity Purification of a Mannose-Binding Protein, a Sensitive Tool in the Diagnostics of igM, via Site-Directed Phosphorylated Mannan Bound to Alumina, J. Chromatogr B Biomed Appl. 9;662(2):191-6 (Dec. 1994).
Kornblum et al., Titanium Dioxide Lakes I: Prepared from Certified Water-Soluble Dyes and Employed in Color-Coating Tablets, J. Pharm Sci 59(7):1016-8 (Jul. 1970).
Kuroda, et al., Phosphopeptide-Selective Column-Switching RP-HPLC With a Titania Precolumn, Anal Sci. 20:1313-1319 (2004).
Lillie et al., Nuclear Stains with Soluble Metachrome Metal Mordant Dye Lakes, Histochemistry 49(1):23-35 (Oct. 1976).
Macri et al., Photocatalytic Oxidation of Methyl-Orange in Aqueous Suspension: Comparison of the Performance of Different Polycrystalline Titanium Oxide, Ann Chim 93(7-8):639-48 (Jul.-Aug. 2003).
Marshall et al., The Determination of Protein Phosphorylation on Electrophoresis Gel Blots by Laser Ablation Inductively Coupled Plasma-Mass Spectrometry, Analyst 127:459-461 (2002).
Marshall et al., The Mechanism of Action of "Mordant" Dyes—A Study Using Preformed Metal Complexes, Histochemie 35(4):361-71 (Jun. 1973).
Martin et al., Strategies and Solid-Phase Formats for the Analysis of Protein and Peptide Phosphorylation Employing a Novel Fluorescent Phosphorylation Sensor Dye, Comb Chem High Throughput Screen 6(4):331-9 (Jun. 2003b).
Martin et al., Quantitative Analysis of Protein Phosphorylation Status and Protein Kinase Activity on Microarrays Using a Novel Fluorescent Phosphorylation Sensor Dye, Proteomics 3(7):1244-1255 (2003).
Meloan et al., Staining of Calcium Deposits with Acid Dyes for Lakes Light and Fluorescence Microscopic Studies, Beitr Pathol. 149(4):386-96 (Sep. 1973).
Mustafa et al., Temperature Effect on Phosphate Sorption by Iron Hydroxide, Environ Technol 25(1):1-6 (Jan. 2004).
Niesen, TP, De Guire, MR, Review: Deposition of Ceramic Thin Films at Low Temperatures from Aqueous Solutions, J. Electroceram. 6:169-207 (2001).
Pinkse, et al., Selective Isolation at the Femtomole Level of Phosphopeptides from Proteolytic Digests Using 2D-NanoLC-ESI-MS/MS and Titanium Oxide Precolumns, Anal Chem. 76:3935-3943 (2004).
Posewitz et al., Immobilized Gallium (III) Affinity Chromatography of Phosphopeptides, Anal Chem. 71(14):2883-92 (Jul. 1999).
Pugniere et al., Immobilization of Enzymes on Alumina by Means of Pyridoxal 5'-Phosphate, Biosci Rep. 8(3):263-9 (Jun. 1988).

Quinn et al., Peroxide-Modified Titanium Dioxide: A Chemical Analog of Putative Martian Soil Oxidants, Orig Life Evol Biosph. 29(1)59-72 (Jan. 1999).
Roegener et al., Ultrasensitive Detection of Unstained Proteins in Acrylamide Gels by Native UV Fluorescence, Anal Chem. 75(1):157-9 (Jan. 2003).
Sano, et al., Chemo-Affinity of Titania for the Column-Switching HPLC Analysis of Phosphopeptides, Anal Sci. 20:565-566 (2004a).
Sano, et al., Titania as a Chemo-affinity Support for the Column-switching HPLC Analysis of Phosphopeptides: Application to the Characterization of Phosphorylation Sites in Proteins by Combination with Protease Digestion and Electrospray Ionization Mass Spectrometry, Anal Sci. 20:861-864 (2004b).
Saquib et al., Photocatalytic Degradation of Two Selected Textile Dye Deriatives, Eosine Yellowish and p-Rosaniline, in Aqueous Suspensions of Titanium Dioxide, J Environ Sci Health Part A Tox Hazard Subst Environ Eng. 38(11):2581-98 (2003).
Schulenberg et al., Analysis of Steady-state Protein Phosphorylation in Mitochondria Using a Novel Fluorescent Phosphosensor Dye, J Biol Chem 278(29):27251-5 (Jul. 2003).
Shimizu et al., A Novel Fluorescent Silica Tracer for Biological Silicification Studies, Chem Biol. 8(11):1051-60 (Nov. 2001).
Steinberg et al., Global Quantitative Phosphoprotein Analysis Using Multiplexed Proteomics Technology, Proteomics 3(7):1128-44 (Jul. 2003).
Tani et al., Investigation of Chromatographic Properties of Titania. I. on Retention Behavior of Hydroxyl and Other Substituent Aliphatic Carboxylic Acids: Comparison with Zirconia, J Liq Chrom and Rel Technologies 22(6):843-856 (1999).
Unlu et al., Difference Gel Electrophoresis: A Single Gel Method for Detecting Changes in Protein Extracts, Electrophoresis 18(11):2071-7 (Oct. 1997).
Vogel et al., Absorption and Fluorescence Spectroscopy of Rhodamine 6G in Titanium Dioxide Nanocomposites, Spectrochimica Acta a Mol Biomol Spectrosc. 60(1-2):245-9 (Jan. 2004).
Wang et al., The Effect of Nanometer Size of Porous Anodic Aluminum Oxide on Adsorption and Fluorescence of Tetrahydroxyflavanol, Spectrochimica Acta A Mol Biomol Spectrosc. 59(6):1139-44 (Apr. 2003).
Wang et al., Quantitative Determination of Proteins at Nanogram Levels by the Resonance Light-Scattering Technique with Macromolecules Nanoparticles of PS-AA, Spectrochim Acta A Mol Biomol Spectrosc. 60(4):747-50 (Mar. 2004).
Wind et al., Spotting and Quantification of Phosphoproteins Purified by Gel Electrophoresis and Laser Ablation-Element Mass Spectrometry with Phosphorus-31 Detection, Electrophoresis 24:1276-1280 (2003).
Wou et al., Effect of Dispersion on the Coloring Properties of Aluminum Dye Lakes, J Pharm Sci 77(10):866-71 (Oct. 1988).
Yezek et al., Adsorption of Sodium Dodecyl Sulfate to Colloidal Titanium Dioxide: An Electrophoretic Fingerprinting Investigation, J Colloid Interface Sci. 1:225(1):227-232 (May 2000).
Yguerabide et al., Resonance Light Scattering Particles as Ultrasensitive Labels for Detection of Analytes in a Wide Range of Applications, J Cell Biochem Suppl. 37:71-81 (2001).
Zeng et al., Adsorptive Removal of Phosphate from Aqueous Solutions Using Iron Oxide Tailings, Water Res. 38:1318-1326 (2004).
Zhou et al., Detection and Sequencing of Phosphopeptides Affinity Bound to Immobilized Metal Ion Beads by Matrix-Assisted Laser Desorption/Ionization Mass Spectrometry, J Am Soc Mass Spectrometry 11(4):273-282 (Apr. 2000).
Nakamura et al., "2D-LC for Selective Detection of Phosphopeptides using Titania Precolumn (Titansphere® TiO)," Chromatography, May 31, 2002, vol. 23, pp. 95-96.
Nakamura et al., "Selective Determination of Phosphorylated Peptides by Column-switching HPLC Equipped with a Titania Precolumn," Oct. 15, 1996, vol. 17, pp. 354-355.
Australian Office Action; Application No. 2005269978; mailed Oct. 1, 2009; pp. 1-2.
Australian Office Action; Application No. 2005269978; mailed Sep. 10, 2008; pp. 1-2.

(56) References Cited

OTHER PUBLICATIONS

European Communication; Application No. 05857278.5-2401; mailed Nov. 9, 2007; pp. 1-13.
European Search Report; Application No. 05857278.5-2401; mailed Jul. 27, 2007; pp. 1-11.
European Search Report; Application No. 05857278.5-2401; mailed Oct. 10, 2008; pp. 1-6.
European Search Report; Application No. 05857278.5-2401; mailed Nov. 6, 2009; pp. 1-3.
European Search Report; Application No. 05857278.5-2401; mailed Dec. 8, 2010; pp. 1-5.
European Search Report; Application No. 05857278.5-2401; mailed Feb. 24, 2012; pp. 1-5.
International Search Report and Written Opinion; PCT/US05/23810; Oct. 26, 2006; pp. 1-8.
Japanese Office Action, Application No. 2007-520439; Dec. 3, 2011; pp. 1-3.
Japanese Office Action; Application No. 2007-520439; Reported Jan. 7, 2011; pp. 1-6.
Siffert and Metzger; "Study of the interaction of titanium dioxide with cellulose fibers in an aqueous medium," *Colloids and Surfaces*, 53, pp. 79-99, 1991.

\* cited by examiner

METHODS AND COMPOSITIONS FOR DETECTING AND ISOLATING PHOSPHORYLATED MOLECULES USING HYDRATED METAL OXIDES

BACKGROUND

The present invention relates to detecting and isolating phosphorylated molecules using phosphoaffinity materials containing one or more hydrated metal oxides, such as yttrium oxide, yttrium aluminum garnet and titanium dioxide.

Cells of the body contain many types of molecules that vary in function, size, lifetime, and numerous other characteristics. Some of these molecules are unchanged during their lifetime within the body, while other molecules become modified through chemical reactions. The modifications can be indicative of particular cell states, including normal states as well as abnormal states caused by injury, infection and disease.

Proteins, for example, are often chemically modified during their lifetime in the body. A protein can be modified during and after its synthesis, or both, and the modification can change the size and the structure of the protein, which in turn can result in changing the protein's function or behavior in the cell. An example of a modification of a protein is the addition of a phosphate group (phosphorylation).

Reversible phosphorylation of threonine, serine, and tyrosine residues on proteins by enzymes called kinases (which add a phosphate) and phosphatases (which remove the phosphate) plays an important role in regulating many cell processes, such as growth and cell cycle control. Phosphorylation can occur sequentially from one protein to another, resulting in a series of activations called a "phosphorylation cascade," which is a type of "signal transduction pathway." Phosphorylation cascades are recognized as signaling networks that direct growth, death, and differentiation of cells—the critical signals for maintaining normal cells in the body. At any given moment in a cell, determination of phosphorylation states of proteins can indicate a signal transduction state, for example an "on" or "off" state of cell growth.

Many cellular processes are regulated by reversible phosphorylation of proteins and upwards of 30% of the total complement of proteins expressed by human cells are likely to be phosphorylated at some point during their existence. Determination of protein phosphorylation state is thus important for identifying protein kinase substrates, as well as revealing the on/off state of signal transduction pathways. The on/off state of signal transduction pathways can be important to understanding pathophysiological processes, such as cancer. To better understand such signal transduction pathways, efforts are underway within the research community to identify phosphorylated proteins of various cell types under different cellular conditions, such as normal and diseased conditions. Determination of differences in phosphorylation that occur under normal and diseased conditions can be used, for example, in development of diagnostic and other medical tests.

Given the important role of phosphorylation in signal transduction pathways, analysis of phosphorylation events that occur within the entire complement of proteins expressed by cells (phosphoproteome analysis), is useful for understanding a range of cellular processes. Phosphoproteome analysis likely will reveal insight into complex biological processes, such as differentiation, growth control and regulated cell death. Accordingly, phosphoproteome analysis is expected to contribute to development of diagnostic and prognostic tests, improve aspects of clinical trials, and provide indications of drug safety and efficacy during drug development.

One challenge in the field of phosphoproteome analysis is developing accurate methods for global evaluation of protein phosphorylation levels. Global analysis of protein phosphorylation is an analytical challenge because signaling phosphoproteins are typically present in low abundance within cells. Analytical methods that improve global analysis of protein phosphorylation can contribute to development of medical tests, such as tests that can simultaneously test for multiple phosphoprotein biomarkers. This type of test is expected to be helpful for detecting diseases and conditions for which single diagnostic markers are unfeasible or unavailable.

Thus, the ability to detect and/or isolate phosphoproteins is useful for cellular research as well as medical test development, given the central role of phosphorylation in many disease processes. Improved approaches for phosphomolecule isolation and detection would accelerate protein phosphorylation global analysis and related general and biomedical phosphomolecule research.

SUMMARY

The technology described herein relates to methods for isolating a phosphomolecule from a sample. In one aspect, method involves (a) contacting a sample with a phosphoaffinity material comprising a hydrated metal oxide, under conditions wherein a phosphomolecule is capable of binding to the phosphoaffinity material to form a phosphomolecule-phosphoaffinity material complex, and (b) separating the phosphomolecule-phosphoaffinity material complex from the sample, thereby isolating the phosphomolecule from the sample. In another aspect, the method involves (a) contacting a sample with a phosphoaffinity material comprising a hydrated metal oxide and a support, under conditions wherein a phosphomolecule is capable of binding to the phosphoaffinity material to form a phosphomolecule-phosphoaffinity material complex, and (b) eluting a phosphomolecule from the phosphomolecule-phosphoaffinity material complex, thereby isolating the phosphomolecule from the sample. These methods further can involve separating the phosphomolecule from the phosphomolecule-phosphoaffinity material complex.

In an embodiment, the invention provides a method for isolating a phosphomolecule from a sample. The method involves (a) contacting a sample with a phosphoaffinity material comprising a hydrated metal oxide, under conditions wherein a phosphomolecule is capable of binding to the phosphoaffinity material to form a phosphomolecule-phosphoaffinity material complex, wherein the hydrated metal oxide comprises yttrium, and (b) separating the phosphomolecule-phosphoaffinity material complex from the sample, thereby isolating the phosphomolecule from the sample. In another embodiment, a method for isolating a phosphomolecule from a sample involves (a) contacting a sample with a phosphoaffinity material comprising a hydrated metal oxide and a support, under conditions wherein a phosphomolecule is capable of binding to the phosphoaffinity material to form a phosphomolecule-phosphoaffinity material complex, wherein the hydrated metal oxide comprises yttrium, and (b) eluting a phosphomolecule from the phosphomolecule-phosphoaffinity material complex, thereby isolating the phosphomolecule from the sample. If desired, unbound sample components can be removed from the phosphomolecule-phosphoaffinity material complex prior to eluting. In an embodiment of these methods, the hydrated metal oxide is yttrium oxide. In another embodiment of these methods, the hydrated metal oxide is yttrium iron garnet.

The invention provides a method for isolating a phosphorylated polypeptide from a sample. The method involves (a) contacting a sample with a phosphoaffinity material comprising a hydrated metal oxide and a support, under conditions wherein a phosphomolecule is capable of binding to the phosphoaffinity material to form a phosphomolecule-phosphoaffinity material complex and in a liquid medium comprising an organic solvent, and (b) eluting a phosphomolecule from the phosphomolecule-phosphoaffinity material complex, thereby isolating the phosphomolecule from the sample. In various embodiments, the liquid medium can include, for example, isopropanol or acetonitrile. In an embodiment, the eluting is performed in the presence of a detergent, such as an ionic detergent.

The invention provides methods for detecting a phosphomolecule in a sample. In an embodiment, the methods involve (a) contacting a sample with a phosphoaffinity material comprising a hydrated metal oxide, under conditions wherein a phosphomolecule is capable of binding to the phosphoaffinity material to form a phosphomolecule-phosphoaffinity material complex, and (b) detecting formation of a phosphomolecule-phosphoaffinity material complex, thereby detecting a phosphomolecule in the sample. In an embodiment, the detecting can involve measuring binding between the phosphomolecule and phosphoaffinity material. In another embodiment, the phosphoaffinity material portion of the phosphomolecule-phosphoaffinity material complex is detected. In a specific embodiment, the metal of the phosphoaffinity material portion is detected. In a further embodiment, the phosphomolecule portion of the phosphomolecule-phosphoaffinity material complex.

The invention provides a variety of commercial packages useful for carrying out a method for isolating and/or detecting a phosphomolecule in a sample. In an embodiment, a commercial package includes a hydrated metal oxide attached to a support, wherein the hydrated metal oxide comprises yttrium. In another embodiment, a commercial package includes a phosphoaffinity unit, the unit comprising a plurality of support sheets coated with a hydrated metal oxide. The support sheet can be, for example, a membrane or paper, such as cellulose. In a further embodiment, a commercial package contains a phosphoaffinity particle comprising a hydrated metal oxide and a detectable agent that binds to the hydrated metal oxide.

In any of the methods and commercial packages described herein, the hydrated metal oxide can be in, for example, particle form. As such, the phosphoaffinity material can comprise a support. The support can be selected from the group of particle, bead, gel, matrix, membrane, filter, fiber, sheet, mesh, frit, resin, sample vessel, column, pipette tip, slide channel and MALDI-TOF plate. The support can include a detectable tag, if desired.

The hydrated metal oxide used in a method of the invention can be selected from the group of aluminum oxide, titanium oxide, yttrium iron garnet, yttrium aluminum garnet, yttrium gallium garnet, ferric oxide, gallium oxide, yttrium oxide, vanadium oxide, zirconium oxide, iron titanate, iron aluminate, calcium titanate, sodium titanate, zirconium aluminate, goethite, gibbsite, bayerite, boehmite, ilmenite, ilmenorutile, pseudorutile, rutile, brookite, pseudobrookite, geikielite, pyrophanite, ecandrewsite, melanostibite, armalcolite, srilankite and anatase. In particular, the metal oxide can be selected from the group of yttrium oxide, yttrium iron garnet and titanium dioxide.

BRIEF DESCRIPTION OF DRAWINGS

FIG. 5A shows a protein profile corresponding to phosphopeptide-containing starting material; FIG. 5B shows a protein profile corresponding to isolated phosphorylated peptide.

FIG. 6A shows a protein profile corresponding to a phosphopeptide-containing starting material; FIG. 6B shows a protein profile corresponding to isolated phosphorylated peptide.

FIG. 7A shows a protein profile corresponding to a phosphopeptide-containing starting material; FIG. 7B shows a protein profile corresponding to isolated phosphorylated peptide.

FIG. 11 shows selective isolation of phosphorylated peptide from a sample containing a phosphorylated peptide and a non-phosphorylated peptide, using a titanium dioxide phosphoaffinity membrane.

FIG. 12 shows selective isolation of phosphorylated peptides from a serum-containing sample using a titanium dioxide phosphoaffinity membrane.

FIG. 13A shows mass spectra of peptides eluted from the phosphoaffinity material, peptides that did not bind (flow-through), and starting material; FIG. 13B shows a mass spectrum corresponding to multiple forms of phosphorylated peptides isolated and detected.

FIG. 14A shows an image of an SDS-PAGE gel of eluted and flow-through fractions; FIG. 14B shows normalized phosphoprotein enrichment ratios.

DESCRIPTION

Figure 1:
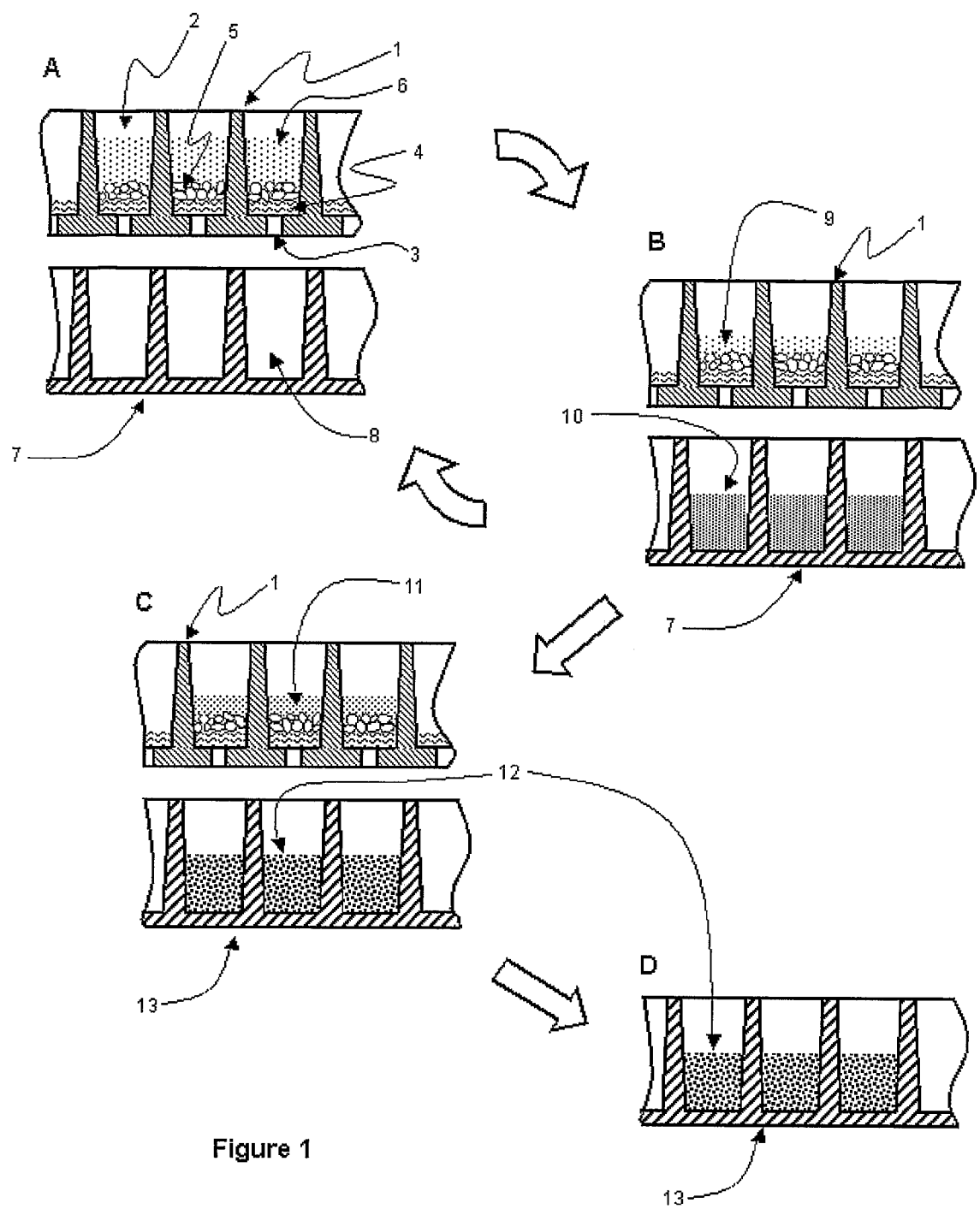
FIG. 1 shows an exemplary process for isolating phosphorylated molecules using hydrated metal oxide particles in a multiwell microplate filtration format.

The technology described herein relates to methods, compositions and commercial packages for isolating and/or detecting phosphorylated molecules using hydrated metal oxide-containing phosphoaffinity materials.

In an embodiment, the present invention is directed to methods for isolating a phosphomolecule. The isolation methods are applicable to preparing populations of different types of phosphomolecules, as well as to preparing a single type phosphomolecule sample. The isolation methods can be used for preparing samples enriched with phosphomolecules, for example to improve detection of phosphomolecules in a complex sample. Isolation of phosphomolecules from a sample can be achieved by binding the phosphomolecules to the phosphoaffinity material and separating the phosphomolecule-phosphoaffinity material complex from the sample. Isolation also can be achieved by binding the phosphomolecule to the phosphoaffinity material, washing away unbound sample components, and eluting phosphomolecules from the phosphoaffinity material. Use of the methods of the invention for preparing isolated phosphorylated polypeptides is described herein, for example, in Examples 1, 2 and 3.

A phosphoaffinity material used in the methods and commercial packages described herein contain, incorporate or are solid forms of a hydrated metal oxide, and the hydrated metal oxide binds selectively to the phosphomolecules. As is described below, a variety of hydrated metal oxides are suitable for binding to phosphomolecules. Example 1 describes individual use of three different phosphoaffinity materials—yttrium oxide, yttrium iron garnet and titanium oxide—for selectively binding to phosphoproteins. Once a complex of the phosphoaffinity material and phosphomolecule is formed, the complex itself can be separated from the sample and/or the phosphomolecule portion of the complex can be separated. As is described herein below, such separations can be carried out using a variety of means, depending on the format selected by the user. For example, when the phosphoaffinity material is in solid particle form or is incorporated into a support, separation can be performed by separating the particle or support (solid or semi-solid phase) from the sample (liquid phase), or visa versa.

The isolation methods described herein can be performed in a variety of physical formats. For example, phosphomolecules can be eluted from column-packed phosphoaffinity materials (see Example 1); phosphomolecules can be eluted from particles packed into wells of a multisample plate (see Example 2); phosphomolecule samples prepared as described in Examples 1 and 2 can be subjected to further purification prior to analysis (see Example 3); and phosphomolecules can be eluted from membranes coated with a phosphoaffinity material (see Examples 5, 7 and 8). Given the examples and guidance provided herein, it will be recognized that a phosphoaffinity material incorporating a hydrated metal oxide can be used in macro, micro, low-throughput and high-throughput formats.

As used herein, the term "isolating" when used in reference to a phosphomolecule means the act of separating the phosphomolecule from other molecules, substances or materials in the sample. The term "isolated" when used in reference to a phosphomolecule, phosphoaffinity material, metal oxide or other component useful in a method or commercial package of the invention means that the component is acted upon by the hand of man to remove other molecules, substances or materials with which the component is associated in a sample or preparation. The term isolated does not require absolute purity, but rather is intended as a relative term. As such, the term isolating includes acting on a sample to increase the amount of phosphomolecules in the sample relative to the amount of one or more initial sample components or amount of initial phosphomolecules, which is sometimes referred to herein as enriching a sample.

A method of the invention can be used for isolating or enriching a phosphomolecule from samples of varying complexity. Examples 1, 2, 5 and 8 describe enrichment of phosphopeptides in samples containing a peptide in phosphorylated state and a non-phosphorylated state; Example 6 describes enrichment of phosphoproteins in a sample containing human serum; Example 7 describes enrichment of phosphopeptides in a sample containing trypsin-digested protein; and Example 8 describes enrichment of phosphoproteins in a sample containing a 5-protein mixture.

As is described in Example 8, the amount of a phosphomolecule in a sample can be enriched by binding the sample to a phosphoaffinity material containing a hydrated metal oxide; removing unbound sample components from the phosphoaffinity material; and eluting phosphomolecules from the phosphoaffinity material. In this specific example, titanium dioxide coated membranes were used as the phosphoaffinity material and phosphoprotein enrichment was determined by comparing the amount of phosphoprotein before and after performing the isolation, relative to the amount of control proteins bovine serum albumin, carbonic anhydrase and myoglobin before and after performing the isolation. Ovalbumin enrichments of 9.5, 8 and 11 relative to BSA, CAH and myo, respectively, were observed in the absence of detergent, while enrichments of 17.7, 8.4 and 125.7, respectively, were observed in the presence of detergent.

In an embodiment, the present invention is directed to methods for detecting a phosphomolecule. Detection of a phosphomolecule in a sample can be achieved by binding the phosphomolecule to a phosphoaffinity material and detecting the complex of the phosphoaffinity material and phosphomolecule, or a portion of the complex. As is described herein below, numerous and diverse analytical methods can be applied to detecting such a complex or a portion of the complex. For example, a physiochemical property of a complex relative to its components, such as mass, charge to mass ratio, refractive index, fluorescence anisotropy and the like can be detected. As another example, a property resulting from the proximity between phosphomolecule and phosphoaffinity material when complexed, such as fluorescence resonance energy transfer and radiometric scintillation proximity-based emission, can be detected. As a further example, a component of the complex, such as the phosphomolecule or the hydrated metal oxide can be detected. Such detecting can involve directly detecting the phosphomolecule or hydrated metal oxide or detecting a tag on the phosphomolecule or hydrated metal oxide. Detection of the metal portion of phosphomolecule-phosphoaffinity material complex is described in Examples 11 and 12.

The detection methods described herein can be performed in a variety of physical formats. For example, phosphomolecules can be detected when in solution; when in a matrix (see Example 10); when in an array (see Example 9); as well as other formats. A variety of particle-based methods for detecting a phosphomolecule are described herein (see, for example, Examples 10 and 11). A phosphoaffinity particle, which can be for example, a hydrated metal oxide or a particle support coated with hydrated metal oxide, can be detected directly; can be labeled prior to detection; or can be used to enrich or isolate a phosphomolecule-phosphoaffinity material complex which is then detected.

The technology described herein involves formation of a complex between a phosphomolecule and a phosphoaffinity material made of, or containing, a hydrated metal oxide. Previous studies have shown that particular phosphomolecules can bind to certain transition metal cations. Inorganic orthophosphates have been shown to adsorb to titanium dioxide particles (Damen et al, 1991; Kim and Chung, 2001). Organic phosphates such as phosphorylated peptides have been shown to bind selectively to titanium dioxide particles, and titanium dioxide particles have been used for enriching phosphoproteins in HPLC techniques (Sano and Nakamura, 2004a, b). Phosphorylated organic compounds, including pyridoxal 5' phosphate-containing and phosphomannose-containing proteins, have been shown to bind selectively to aluminum oxide particles (Pugniere et al., 1988; Coletti-Previero and Previero, 1989; Koppel et al, 1994). Iron (III) oxyhydroxide particles have been shown to adsorb phosphate-containing compounds and have been used in treatment of industrial waste water (Zeng et al, 2004; Mustafa et al, 2004). Monoesters of phosphoric acid and phosphonic acids have been shown to bind to hydrated metal oxides over a wide pH range. D,L-serine-O-phosphate, ethanolamine-O-phosphate and phenylphosphonic acid have been shown to bind selectively to hydrated aluminum oxide (Coletti-Previero and Previero, 1989) and adenosine 5'-phosphate has been shown to bind selectively to aluminum oxide (Colefti-Previero and Previero, 1989). Immobilized metal affinity chromatography (IMAC) uses a stationary phase containing organic chelating groups charged with trivalent transition metal ions, such as Ga (III) and Fe(III), to enrich phosphopeptides prior to microchemical analysis (Posewitz and Tempst, 1999). For IMAC, peptides are eluted from the resin using a buffer having higher pH or higher concentration of inorganic phosphate with respect to the sample loading buffer.

An example of a commercial IMAC-based procedure is the IMAP assay (Molecular Devices, Sunnyvale, Calif.). IMAP is a fluorescence polarization homogenous solution assay in which beads derivatized with trivalent transition metal ions are used for binding to phosphate residues. The beads are added to a kinase reaction along with a fluorescently-labeled peptide substrate. If the kinase phosphorylates the substrate, the bead binds to the phosphate residue. Rotation of the fluorescent phosphorylated substrate is slowed by the bead binding, resulting in greater polarization of the emitted light. IMAP appears to be applicable to measurement of phosphopeptides but not phosphoproteins. In IMAP, fluorescence polarization readings are performed at a pH value of less than about 6.0 to preserve interaction of the phosphate group with the trivalent cation. Consequently, continuous monitoring of kinase assays cannot be achieved by IMAP because kinase reactions are typically inhibited at the low pH at which fluorescence polarization is read.

The technology described herein for isolating and/or detecting phosphomolecules differs from isolation methods using IMAC, in that the present technology employs a hydrated metal oxide, rather than a chelated trivalent transition metal cation. The hydrated metal oxide used in the present technology can be presented to a sample in various forms, including particles and films. Such particles and films differ from metal ions in their physical properties, such as their characteristic surface plasmon absorption bands. As another example, whereas metal ions do not have isoelectric points, hydrated metal oxide particles and surfaces have isoelectric points. The mechanism of phosphate moiety-metal oxide interactions on surfaces is thought to involve physiochemical phenomenon different from interaction with transition metal ions. Without wishing to be bound by theory, it appears that interaction of phosphate moieties with hydrated metal oxide occurs via an ion exchange sorption-type mechanism in which exchange of hydroxide anions on the surface of the metal oxide with phosphate moieties mediate the sorption. For this reason, experimental conditions for hydrated metal oxide interaction with phosphate moieties can differ from immobilized metal ion interaction with phosphate moieties. In particular, hydrated metal oxide phosphoaffinity materials do not involve loading metal ions onto an affinity material and do not leach metal ions during use. In addition, devices made from hydrated metal oxides can be rugged and autoclavable.

The technology described herein relates to methods for isolating a phosphomolecule from a sample. In one aspect, method involves (a) contacting a sample with a phosphoaffinity material comprising a hydrated metal oxide, under conditions wherein a phosphomolecule is capable of binding to the phosphoaffinity material to form a phosphomolecule-phosphoaffinity material complex, and (b) separating the phosphomolecule-phosphoaffinity material complex from the sample, thereby isolating the phosphomolecule from the sample. In another aspect, the method involves (a) contacting a sample with a phosphoaffinity material comprising a hydrated metal oxide and a support, under conditions wherein a phosphomolecule is capable of binding to the phosphoaffinity material to form a phosphomolecule-phosphoaffinity material complex, and (b) eluting a phosphomolecule from the phosphomolecule-phosphoaffinity material complex, thereby isolating the phosphomolecule from the sample. These methods further can involve separating the phosphomolecule from the phosphomolecule-phosphoaffinity material complex.

In an embodiment, the invention provides a method for isolating a phosphomolecule from a sample. The method involves (a) contacting a sample with a phosphoaffinity material comprising a hydrated metal oxide, under conditions wherein a phosphomolecule is capable of binding to the phosphoaffinity material to form a phosphomolecule-phosphoaffinity material complex, wherein the hydrated metal oxide comprises yttrium, and (b) separating the phosphomolecule-phosphoaffinity material complex from the sample, thereby isolating the phosphomolecule from the sample. In another embodiment, a method for isolating a phosphomolecule from a sample involves (a) contacting a sample with a phosphoaffinity material comprising a hydrated metal oxide and a support, under conditions wherein a phosphomolecule is capable of binding to the phosphoaffinity material to form a phosphomolecule-phosphoaffinity material complex, wherein the hydrated metal oxide comprises yttrium, and (b) eluting a phosphomolecule from the phosphomolecule-phosphoaffinity material complex, thereby isolating the phosphomolecule from the sample. If desired, unbound sample components can be removed from the phosphomolecule-phosphoaffinity material complex prior to eluting. In an embodiment of these methods, the hydrated metal oxide is yttrium oxide. In another embodiment of these methods, the hydrated metal oxide is yttrium iron garnet.

The invention provides a method for isolating a phosphorylated polypeptide from a sample. The method involves (a) contacting a sample with a phosphoaffinity material comprising a hydrated metal oxide and a support, under conditions wherein a phosphomolecule is capable of binding to the phosphoaffinity material to form a phosphomolecule-phosphoaffinity material complex and in a liquid medium comprising an organic solvent, and (b) eluting a phosphomolecule from the phosphomolecule-phosphoaffinity material complex, thereby isolating the phosphomolecule from the sample. In various embodiments, the liquid medium can include, for example, isopropanol or acetonitrile. In an embodiment, the eluting is performed in the presence of a detergent, such as an ionic detergent.

The invention provides methods for detecting a phosphomolecule in a sample. In an embodiment, the methods involve (a) contacting a sample with a phosphoaffinity material comprising a hydrated metal oxide, under conditions wherein a phosphomolecule is capable of binding to the phosphoaffinity material to form a phosphomolecule-phosphoaffinity material complex, and (b) detecting formation of a phosphomolecule-phosphoaffinity material complex, thereby detecting a phosphomolecule in the sample. In an embodiment, the detecting can involve measuring binding between the phosphomolecule and phosphoaffinity material. In another embodiment, the phosphoaffinity material portion of the phosphomolecule-phosphoaffinity material complex is detected. In a specific embodiment, the metal of the phosphoaffinity material portion is detected. In a further embodiment, the phosphomolecule portion of the phosphomolecule-phosphoaffinity material complex.

A phosphomolecule can be isolated and/or detected from a variety of types of samples using the technology described herein. As used herein, the term "sample" means a substance that contains or is suspected of containing a phosphorylated molecule. A sample useful in a method of the invention for isolating and/or detecting a phosphorylated molecule can be a liquid or solid, can be dissolved or suspended in a liquid, can be in an emulsion or gel, and can be bound to or absorbed onto a material. A sample can be a biological sample, environmental sample, experimental sample, diagnostic sample, or any other type of sample that contains or is suspected to contain a phosphorylated molecule. As such, a sample can be, or can contain, an organism, organ, tissue, cell, bodily fluid, biopsy sample, or fraction thereof. A sample useful in a method of the invention can be any material that is suspected to contain phosphorylated molecules, such as substrates of kinases and phosphatases. In a biological context, a sample can include biological fluids, whole organisms, organs, tissues, cells, microorganisms, culture supernatants, subcellular organelles, protein complexes, individual proteins, recombinant proteins, fusion proteins, viruses, viral particles, peptides and amino acids.

A sample can be processed to preserve or stabilize phosphorylated molecules. Methods for preserving the integrity of molecules in a sample are well known to those skilled in the art. Such methods include the use of appropriate buffers and/or inhibitors, including nuclease, protease and phosphatase inhibitors that preserve or minimize changes in the molecules in the sample. Such inhibitors include, for example, chelators such as ethylenediamne tetraacetic acid (EDTA), ethylene glycol bis(P-aminoethyl ether)N,N,N1,NI-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for allowing selective interactions between molecules are well known to those skilled in the art and can be varied depending, for example, on the type of molecule in the sample to be characterized (see, for example, Ausubel et al., Current Protocols in Molecular Biology (Supplement 47), John Wiley & Sons, New York (1999); Harlow and Lane, Using Antibodies: A Laboratory Manual, Cold Spring Harbor Press (1999); Tietz Textbook of Clinical Chemistry, 3rd ed., Burtis and Ashwood, eds., W.B. Saunders, Philadelphia, (1999)).

A sample also can be processed to reduce the presence of interfering substances and/or reduce non-selective binding of sample components to a phosphoaffinity material. Exemplary agents useful for improving solubility of phosphorylated molecules include detergents such as TRITON X-100, sodium deoxycholate, urea, thiourea and sodium dodecyl sulfate. A tendency of acidic polypeptides to bind to phosphoaffinity materials non-selectively can be reduced by methyl esterification of the polypeptide sample (Ficarro et al, 2002; Brill et al, 2004).

A sample can be fractionated prior to use in a method of the invention if desired. Well known fractionation methods such as immunoprecipitation, 1-D gel electrophoresis, 2-D gel electrophoresis, electroblotting, liquid chromatography, electrochromatography, dialysis, two-phase polymer separations and solid phase extraction can be used for sample fractionation. Various methods for fractionating a fluid sample or cell extract are well known to those skilled in the art, including subcellular fractionation or chromatographic techniques such as ion exchange, hydrophobic and reverse phase, size exclusion, affinity, hydrophobic charge-induction chromatography, and the like (Ausubel et al., supra, 1999; Scopes, Protein Purification: Principles and Practice, third edition, Springer-Verlag, New York (1993); Burton and Harding, J. Chromatoqr. A 814:71-81 (1998)).

A sample can be labeled with a tag prior to use in a method of the invention. Examples of tags include detectable moieties, such a luminescent moieties, fluorescent moieties, radioactive moieties and the like; purification tags such as polyhistidine, flag, myc and GST tags; polynucleotide tags, aptamers, protein nucleic acids; biological tags such as phage; antibody and antibody-like tags; reactive organic molecule or peptide mass tags or other mass tags such as particles of defined size, for example, metal beads and nanoparticle tags, and the like. Example 11 describes labeling of a sample with a fluorescent moiety. In this example, detection of a phosphomolecule is performed by detecting fluorescence quenching of the phosphomolecule tag.

A phosphoaffinity material useful in a method of the invention for isolating and/or detecting a phosphomolecule or commercial package contains or is a hydrated metal oxide that binds selectively to a phosphomolecule. Exemplary hydrated metal oxides include hydrated forms of yttrium oxide ($Y_2O_3$), iron oxide ($Fe_2O_3$, $Fe_3O_4$), yttrium iron garnet ($Fe_5O12_Y_3$), yttrium gallium garnet ($Y_3Ga_5O1_2$), yttrium aluminum garnet ($Y_3Al_5O_{12}$), vanadium oxide ($VO_2$), zirconium oxide ($ZrO_2$), iron titanate ($Fe_2Ti_2O7$), iron aluminate ($FeAl_2O_5$), calcium titanate ($CaTiO_3$), sodium titanate ($Na_2TiO_3$), and zirconium titanium aluminate ($ZrTi_2Al_2O_5$). Hydrated metal oxides also include composites of cores of hematite, magnetite, chromium hydroxide or titanium dioxide, with surface coatings such as alumina, titanium dioxide, zirconia and yttria. Mineral oxides are widely distributed in nature and are often present as suspended particles in aqueous environments. Chemical processes, such as sorption phenomena, are determined in part by surface properties of the particles at the metal oxide-water interface. A number of naturally occurring mineral oxides, such as goethite ($\alpha$-FeOOH), gibbsite ($\alpha$-Al(OH)$_3$), bayerite ($\beta$-Al(OH)$_3$), boehmite ($\gamma$-Al(OH)$_3$), ilmenite (FeTiO$_3$), ilmenorutile (Fex(Nb, Ta)$_2$x.$_4$Ti1-x$O_2$), pseudorutile (Fe$_2$Ti$_3$O$_9$), rutile (TiO$_2$), brookite (TiO$_2$), pseudobrookite (Fe$_2$TiO$_5$), geikielite (MgTiO$_3$), pyrophanite (MnTiO$_3$), ecandrewsite (Zn, Fe, Mn)TiO$_3$, melanostibite (Mn (Sb, Fe)O$_3$), armalcolite (Mg, Fe)Ti$_2$O5, srilankite (Ti, Zr)O$_2$ and anatase (TiO$_2$), can be used in a phosphoaffinity material for selective binding to phosphomolecules. In general, these and other inorganic metals, when hydrated, present a surface that is covered with a layer of a metal oxide, hydroxide or oxohydroxidehydroxyl groups which contribute to their overall physicochemical properties, including their ability to adsorb phosphorylated molecules. In an embodiment, a phosphoaffinity material useful in the methods and commercial packages of the invention contain a hydrated metal oxide selected from the group of aluminum oxide, titanium oxide, yttrium iron garnet, yttrium aluminum garnet, yttrium gallium garnet, ferric oxide, gallium oxide, yttrium oxide, vanadium oxide, zirconium oxide, iron titanate, iron aluminate, calcium titanate, sodium titanate, zirconium titanium aluminate, goethite, gibbsite, bayerite, boehmite, ilmenite, ilmenorutile, pseudorutile, rutile, brookite, pseudobrookite, geikielite, pyrophanite, ecandrewsite, melanostibite, armalcolite, srilankite and anatase. In specific embodiments, the hydrated metal oxides are yttrium oxide, yttrium iron garnet and titanium dioxide (see, for example, Example 1). In a particular embodiment, the selected hydrated metal oxide is not titanium dioxide, such as a non-titanium hydrated metal oxide. In other embodiments, the selected hydrated metal oxide is not iron oxide and not aluminum oxide.

A phosphoaffinity material selected for use in a method or commercial package of the invention for isolating and/or detecting a phosphomolecule is capable of binding to a phosphomolecule. A phosphomolecule can be a macromolecule, such as a polypeptide and polynucleotide, as well as a small molecule, such as an amino acid and nucleotide. Non-limiting examples of molecules that can contain a phosphorylated moiety include an amino acid, a peptide, a polypeptide, a nucleotide, a polynucleotide, a lipid, glycan and a carbohydrate. A phosphorylated moiety present on a phosphorylated polypeptide, such as a protein or peptide, can be phosphoserine, phosphothreonine, phosphotyrosine, 1-phosphohistidine, 3-phosphohistidine, phosphoaspartic acid, phosphoglutamic acid, Nε-phospholysine, delta-O-phosphohydroxylysine, Nω-phosphoarginine, thiophosphorylation, phosphocysteine, pyridoxal phosphate Schiff base conjugated to the ε-amino group of lysine, N-acetylglucosamine 1-phosphate modified serine, mannose 6-phosphate present in asparagine-linked oligosaccharides or O-pantetheine phosphorylated serine. Phosphomolecules isolated and/or detected using a method of the invention include molecules containing one or more phosphomimetic groups. Non-limiting examples of phosphomimetic groups include O-boranophosphopeptides and O-dithiophosphopeptides, derivatized on tyrosine, serine, or threonine residues, phosphoramide, H-phosphonate, alkylphosphonate, phosphorothiolate, phosphodithiolate and phosphorofluoridate. Selective binding means that the phosphoaffinity material binds to one or more phosphomolecules but does not substantially bind to non-phosphomolecules.

It is understood that a particular phosphoaffinity material used in a method or commercial package of the invention can be capable of selective binding to phosphomolecules, or to a subset of these types of molecules, such as selective binding to phosphorylated polypeptides, as well as to particular phosphorylated moieties. As an example of selective detection of a particular phosphorylated moiety, detection of phosphotyrosine residues on a phosphorylated polypeptide is described in Example 9.

A sample or phosphoaffinity material used in a method or commercial package of the invention can be attached to a support. As used herein, the term "support" means a solid or semi-solid material onto which a metal oxide, sample or phosphomolecule can be deposited, attached immobilized, entrapped, captured or coated, or which can be functionalized to include a metal oxide, sample or phosphomolecule. A support can be a natural or synthetic material, and can be an organic or inorganic material, such as a polymer, resin, metal or glass. Suitable supports are known in the art and illustratively include an agarose, such as is commercially available as Sepharose; a cellulose, illustratively including a carboxymethyl cellulose; a dextran, such as is commercially available as Sephadex; a polyacrylamide; a polystyrene; a polyethylene glycol; a resin; a silicate; divinylbenzene; methacrylate; polymethacrylate; glass; ceramics; paper; metals; metalloids; polyacryloylmorpholide; polyamide; poly(tetrafluoroethylene); polyethylene; polypropylene; poly(4-methylbutene); poly(ethylene terephthalate); rayon; nylon; poly(vinyl butyrate); polyvinylidene difluoride (PVDF); silicones; polyformaldehyde; cellulose acetate; cotton; wool; dextran; Trisacryl; hydroxyalkyl methacrylate, poly(vinylacetate-co-ethylene), oxirane acrylate, polyethylene, polypropylene, poly(vinyl chloride), poly(methyl methacrylate), phenol resin, poly(vinylidene difluoride), poly(ethylene terephthalate), polyvinylpyrrolidone, polycarbonate, starch, nitrocellulose; mixtures thereof, and the like.

A support useful in a method of the invention can have a variety of physical formats, which can include for example, a membrane, column, a hollow, solid, semi-solid, pore or cavity containing particle such as a bead, a gel, a fiber, including a fiber optic material, a sheet, a matrix and sample receptacle. Non-limiting examples of sample receptacles include sample wells, tubes, capillaries, vials and any other vessel, groove or indentation capable of holding a sample, including those containing membranes, filters, matrices and the like. A sample receptacle can be contained on a multi-sample platform, such as a microplate, slide, microfluidics device, array substrate, mass spectrometry sample plate, and the like. A particle to which a phosphoaffinity material is attached can have a variety of sizes, including particles that remain suspended in a solution of desired viscosity, as well as particles that readily precipitate in a solution of desired viscosity. In particular embodiments, a particle support or phosphoaffinity material particle such as a crystal have diameters of between about 1 nm and 1 μm. The term "phosphoaffinity particle" means a phosphoaffinity material in particle form. The term encompasses particles coated with a phosphoaffinity material as well as particles made of a phosphoaffinity material, such as a crystal or other solid form. The term "phosphoaffinity sheet" means a phosphoaffinity material in flat form, such as a paper, membrane, filter, and the like. A phosphoaffinity material can be part of or incorporated into a device, such as for example, a spin-column, microcolumn pipette tip, multi-well microwell strip, multi-well microplate and magnetic separator. A support can also contain a ferromagnetic or paramagnetic substance, for example, when magnetic separation procedures are employed.

If desired, a support can include a tag, such as a tag useful for detection and/or purification. A support also can be an inherent characteristic of a hydrated metal oxide, such as a metal oxide particle, crystal or other solid form. For use as a phosphoaffinity material in column, bed or surface form, the support can have characteristics such as uniform porous network and chemical and/or biological inertness.

A variety of procedures can be used for attaching or depositing a metal oxide onto a support for preparing a phosphoaffinity material useful in a method or commercial package of the invention. For example, the metal oxide can be deposited on the support through liquid-phase deposition, chemical bath deposition, successive ion layer adsorption and reaction (SILAR), electroless deposition, reactive sputtering, reactive evaporation, spray pyrolysis, track-etching, anodic oxidation, cold-press molding, chemical vapor deposition, or sol-gel processing. The deposited metal oxide can be crystalline, nanocrystalline, poorly crystallized or amorphous. In some embodiments, a crystalline layer is subsequently hydroxylated to render it suitable for binding phosphorylated molecules, and the crystalline layer can be hydroxylated by incubation in an aqueous-based medium for a period of time, such as, for example, one hour to several months.

In an embodiment, a metal oxide is attached to a support at about ambient temperature and in an aqueous-based medium. In this embodiment, an organic support material is generally employed. Non-limiting examples of organic support materials include cellulose, cotton, wool, dextran, agarose, polyacrylamide, Trisacryl, hydroxyalkyl methacrylate, poly(vinylacetate-co-ethylene), oxirane acrylate, polyethylene, polypropylene, poly(vinyl chloride), poly(methyl methacrylate), phenol resin, poly(vinylidene difluoride), poly(ethylene terephthalate), polyvinylpyrrolidone, polycarbonate and starch. Deposition can be achieved on an ion-by-ion or particle attachment basis. Functionalization of the organic support, such as with sulfonate, hydroxyl or carboxyl groups can aid in depositing the metal oxide. In one embodiment, the hydrated metal oxide is deposited on to a support of cellulose or modified cellulose. Therefore, in an embodiment, an organic support used in a method or commercial package of the invention is functionalized with organic groups, while in other embodiments, the organic support is functionalized with sulfonate, hydroxyl or carboxyl groups.

In an embodiment, a hydrated metal oxide is deposited or attached to an inorganic support. Exemplary inorganic supports include ceramic, metal, glass, alumina, silica, zirconia, a ferromagnetic material and a paramagnetic material. More durable porous ceramic-based supports, such as alumina, permit derivatization with hydrated metal oxides using harsher conditions. Ceramic membranes can be useful for certain biomedical applications because they are generally inert towards various harsh chemicals (strong acids and organic solvents) and high temperatures. For example, hydrated metal oxides are known to adsorb silicate species from solution when they are stored in glass at neutral to basic pH values, resulting in a substantial decrease in isoelectric point of the material. One approach to removing adsorbed material from hydrated metal oxides is to wash them with 1 M sodium hydroxide, deionized water, 1 M nitric acid and then again with deionized water. Whether an organic or inorganic support is employed, the hydrated metal oxide binds to the phosphomolecule with sufficient affinity to allow detection of the complex, and is stable over the time of assay performance.

One approach to preparing a porous hydrated metal oxide involves low-temperature synthesis of thin films through direct deposition from aqueous-based solutions using Ti (IV), Fe (III), Zr (IV) or Al (III) ions as precursors for the formation of hydrated metal oxide coatings (Niesen and De Guire, 2001). These metal ions can be used for this general approach because they are readily hydrolyzed, even in acidic aqueous-based media. Similar coatings can be prepared using alternative solvents, such as 2-propanol or appropriately formulated blends of acetic acid, acetone and water, without damaging the underlying organic support. Aqueous-based solutions of 0.03 to 0.1 M titanium tetrafluoride in the pH range of 1.0 to 3.1 at 40 to 70 degrees centigrade can be used for deposition of anatase films on both organic and inorganic substrates. Particularly, 0.05 M titanium tetrafluoride at pH 1.9 can be used for coating organic supports at 60 degrees centigrade.

Without wishing to be bound by theory, it appears that heterogeneous nucleation of titanium dioxide is required for effective coating of supports. Since titanium-fluoride bonds are relatively stable, hydrolysis and polymerization of the reactant occurs at a relatively slow rate. At pH values above 3.1, homogenous nucleation of supersaturated solutions predominates and precipitation results. Below pH values of 1.0, titanium tetrafluoride appears to form a metastable solution with a slow reaction rate. Heterogeneous nucleation occurs at intermediate conditions between the metastable and supersaturated states. A phase diagram of the metal oxide starting material concentration versus pH for a given temperature can be used for determining appropriate reaction conditions for a variety of suitable starting materials, including monomeric titanium tetrafluoride, titanium lactate, titanium tetraisopropoxide, and titanium tetrabutoxide.

Once the reaction conditions for heterogeneous nucleation using the above-described or different metal oxide starting materials are determined, the support can be incubated in the appropriate deposition solution, generally for a period of 0.5 to 260 hours, depending on the desired coating thickness, particular metal oxide and material to be coated. The diameter of the particles in the films typically increases gradually throughout the deposition time course. Incubation time can be adjusted to achieve a desired layer thicknesses, such as a thickness of 200 nm or less. Particle sizes in the films typically range from a few nanometers to a few tens of nanometers.

Optionally, a surfactant can be included in the deposition solution to reduce any cracking or crazing resulting from bending stress applied to the organic support subsequent to manufacture of the membranes. Non-limiting examples of surfactants that can be employed for this purpose, as well as for other purposes employing detergents as described throughout the present application, include sodium dodecyl sulfate, lithium dodecyl sulfate, sodium bis-2-ethylhexylsulphosuccinate, sodium cholate, perfluordecyl bromide, cetyltrimethylammonium bromide, didodecylamonium bromide, Triton X-100, polyoxyethylene 10-oleyl ether, polyoxyethylene-10-dodecyl ether, N,N-dimethyldodecylamine-N-oxide, Brij 35, Tween-20, Tween-80, sorbitan monooleate, lecithin, diacylphosphatidylcholine, sucrose monolaurate and sucrose dilaurate. A binder can be included in an aqueous- or organic-based metal oxide deposition solution. The binder can be, for example, polyvinyl alcohol, polyethylene glycol, polyethyleneimine, poly(dimethylsiloxane), hydroxypropylcellulose and polyacrylamide. For metal oxides, generally hydrophilic supports can have more favorable coating performance characteristics than hydrophobic ones, because binding of metal oxide particles appears to involve formation of hydrogen bounds or bridging oxygen atoms through a dehydration reaction between the particles and the underlying substrate.

To remove excess fluoride that can remain affixed to a hydrated metal oxide surface when using fluoride-containing starting materials in deposition solutions, an aqueous-based solution containing fluoride scavengers, such as boric acid, can be employed. In some embodiments, titanium tetrafluoride, titanium lactate, titanium tetraisopropoxide and/or titanium tetrabutoxide can serve as precursor metal ions for deposition of hydrated metal oxides onto a support. Aqueous-based solutions containing 0.03 to 0.1 M titanium tetrafluoride in the pH range of 1.0 to 3.1 and in the temperature range of 40 to 70° C. can be employed for deposition of the hydrated metal oxides onto the scaffolding. In embodiments, an aqueous-based solution comprising 0.05 M titanium tetrafluoride at pH 1.9 and at 60° C. is employed for deposition of the hydrated metal oxides onto the support.

In another liquid-phase deposition approach, hydrated metal oxide or hydroxide thin films can be formed by the ligand-exchange (hydrolysis) equilibrium reaction of metal-fluoro complex ionic species and a fluoride consumption reaction using boric acid or aluminum metal (Niesen and De Guire, 2001). Using this technique, thin films can be formed on a variety of organic substrates by immersing the supports directly in the deposition solution. Aqueous solutions of ammonium titanium fluoride (($NH_4$)$_2$$TiF_6$) and boric acid ($H_3BO_3$), for example, can be used for coating organic supports with titanium dioxide using this approach. Similar coatings can be produced for vanadia, iron oxyhydroxide, zirconia and multicomponent films containing more than one hydrated metal oxide (Niesen and De Guire, 2001).

In addition to liquid phase deposition, aqueous-based methods such as chemical bath deposition, successive ion layer adsorption and reaction (SILAR), and electroless deposition can be employed to coat supports with hydrated metal oxides (Niesen and DeGuire, 2001). As another alternative to the liquid-phase deposition approaches described above, coating can be performed by mixing of metal oxide powder with a solution containing an appropriate binder, such as polyvinyl alcohol, polyethylene glycol, polyethyleneimine, poly(dimethylsiloxane), hydroxypropylcellose or polyacrylamide, and then depositing the material on a ceramic support as a thin film. Additionally, hydrated metal oxide coatings can be prepared by a range of other deposition techniques, including reactive sputtering, reactive evaporation, spray pyrolysis, track-etching, anodic oxidation, cold-pressed molding, chemical vapor deposition and sol-gel processing. In general, these methods require a heating process at relatively high temperatures, above 400 degrees centigrade, to obtain sufficient crystallinity. Ceramic-based membranes, for example, can be fabricated using these and other approaches.

Crystalline hydrated metal oxide coatings have been described. For example, titanium dioxide thin films have been used as antibacterial coatings, as deodorization disinfection sheets, for soil-proofing household furnishings, as anti-algal oil-proofing plates, as antifogging coatings, as deodorant fibers, and as a low-cost light-harvesting composite material for solar cells (Niesen and De Guire, 2001).

Crystallinity of hydrated metal oxide surfaces can be a useful characteristic for certain uses of metal oxide-coated membranes mentioned above. Hydrated metal oxides can be nano-porous include ultrafine crystallites or be poorly crystallized, as long as the affinity surface contains numerous hydroxide groups. The act of sintering the metal oxide surface at elevated temperatures, such as at temperatures greater than 300 degrees centigrade, is expected to be detrimental to the envisioned application, as this will reduce the extent of interaction between the metal oxide and the phosphorylated molecules, due to a loss of pendant hydroxyl groups on the oxide surface. Thus, when sintered metal oxide surfaces are employed, a procedure for regenerating the hydroxylated surface is generally employed after the heating process. A procedure for recovering hydroxyl groups involves incubating the metal oxides in an aqueous environment for an extended period of time.

The methods described herein are carried out under conditions that allow a phosphomolecule to bind a phosphoaffinity material to form a phosphomolecule-phosphoaffinity material complex. A phosphomolecule generally will bind to a phosphoaffinity material under typical protein interaction assay conditions. Such conditions are well known to those skilled in the art and generally include roughly physiologically salt levels, a buffering agent, and a temperature in the range of 4-37 degrees C. For a chosen phosphoaffinity material, a sample can be adjusted or placed into a solution or environment to have a specified characteristic such as a specified pH, salt concentration, surfactant property, viscosity and the like. The ability of a phosphomolecule to bind selectively to a phosphoaffinity material can be improved, enhanced and/or stabilized in the presence of sample ingredients such as inorganic salts, alcohols, detergents and surfactants, if desired. In an embodiment of a method of the invention, a sample contacted with a phosphoaffinity material in the presence of a detergent. In a specific embodiment, the detergent is an ionic detergent such as SDS. A variety of detergents can be used when contacting a sample with a phosphoaffinity material. The detergent can be anion, cationic, zwitterionic or non-ionic. Those skilled in the art will be able to select a suitable detergent for use with a particular sample and phosphoaffinity material. Example 7 describes use of an ionic detergent during sample incubation with phosphoaffinity material, and use of non-ionic detergent during phosphopeptide elution from the phosphoaffinity material.

The ability of a phosphomolecule to bind selectively to a phosphoaffinity material containing a hydrated metal oxide can be modulated by pH if desired. In aqueous-based media the predominant surface functional group on metal oxides is the hydroxyl group. Without wishing to be bound by theory, it appears that hydroxyl groups of hydrated metal oxides are polarized and electrically charged and this state allows interaction with phosphorylated molecules under certain pH conditions. The oxide surface adsorbs and/or desorbs protons from solution, thus influencing the surface charge. This induces electrostatic effects in the vicinity of the charged surface, which can affect the capacity of the metal oxide for sorption of different ionic species from the aqueous-based media. At low pH values the surface charge becomes positive, while at high pH values it becomes negative. The pH value at which the particles possess no surface charge is referred to as the isoelectric point or pH of zero zeta potential. The loss or gain of protons is commonly considered as an acid-base reaction at the metal oxide surface. A variety of different surface hydroxyl groups can be present on a metal oxide surface. When a surface hydroxyl group is coordinated to a single metal atom, it is referred to as a singly coordinated or terminal hydroxyl group, whereas if the hydroxyl group is coordinated to two, three or four metal atoms, it is referred to as a bridging hydroxyl group. For iron oxides, the surface hydroxyl groups can be coordinated to one, two or even three underlying metal atoms. Two surface hydroxyl groups can also be bound to a single metal atom. The configurations of the different types of surface groups depend upon the structure of the oxide and the crystal face being examined, with different surface groups likely to display different chemical properties. Adsorption of phosphorylated molecules occurs by complex formation reactions between the dissolved phosphorylated solute and the titratable surface functional groups of the hydrated metal oxide surface. Those skilled in the art will be able to empirically confirm an appropriate pH for use of a particular hydrated metal oxide.

In the case of titanium dioxide surfaces, protonation and consequently positive charge attributes are achieved below the material's isoelectric point of approximately 6.0. Other metal oxide surfaces differ in the isoelectric point that is conducive to the generation of a proper surface for affinity capture of phosphorylated molecules. For example, hydrated zirconia possesses an isoelectric point of 8.2, while hematite, yttrium oxide, and gibbsite possess isoelectric point values of 7.5, 8.5, and 10.0, respectively. Inclusion of certain alkali metals in the media can shift the isoelectric point of hydrated metal oxide particles to higher pH values, as observed with rutile particles incubated with barium, calcium or magnesium salts. The isoelectric point of hydrated metal oxides can also be shifted depending on the preparation method, trace impurities and the degree of hydration, and the like. Overall, metal oxides of the general formula $Me_2O_3$ typically have isoelectric points of about 9.0. Metal oxides of the general formula $MeO_2$ typically have isoelectric points that increase with the metal atom ionic radius and with decreasing electronegativity of the metal atom. These factors can be useful to those skilled in the art for determining conditions for isolating and/or detecting phosphomolecules.

For example, the isoelectric point of the hydrated metal oxide can establish an upper limit for pH of a sample solution used when forming a phosphomolecule-phosphoaffinity material complex. Reciprocally, elution can be favored at pH values above the isoelectric point of the hydrated metal oxide. When using membranes or filters containing amorphous or weakly crystallized hydrated metal oxides, strongly acidic (pH<3.0) and strongly basic (pH>11.0) solutions can cause chemical instability of the hydrated metal oxide surface. Those skilled in the art will be able to confirm the integrity of membranes, filters and other supports processed under various pH conditions.

The adsorption of alkali or alkaline-earth metal cations can be useful for regulating binding of a hydrated metal oxide to a phosphomolecule. Exemplary metal cations useful for this purpose include Ba (II), Mg (II), and Ca (II).

In certain embodiments of the present invention, a phosphomolecule isolated and/or detected using a method of the invention is contained in a sample solution. In other embodiments of the present invention, the phosphomolecule is contained on a support. If desired, one or more types of phosphomolecule can be presented on a support while other types are presented in solution. Methods for attaching a phosphomolecule to a support are well known to those skilled in the art, and are exemplified herein below.

Methods described herein can involve separating a phosphomolecule-phosphoaffinity material complex from a sample, thereby isolating the phosphomolecule from the sample. Separation of the phosphomolecule-phosphoaffinity material complex can be achieved by a variety of well known means. In certain embodiments, a phosphomolecule and/or a sample (i.e. a phosphomolecule contained in the sample) can be attached to a support. When a portion of a phosphomolecule-phosphoaffinity material complex is attached to a support, a separation can be performed by removing a liquid phase from the support and/or by washing the support to remove a liquid phase, gel, colloidal, or other type of non-liquid phase from the support. The separation can occur in a variety of formats, such as column, membrane, particle separation by gravity, vacuum, magnetic or other force, and the like. Similarly, in a certain embodiment, the hydrated metal oxide is a particle, and separation can be carried out by a particle separation. Alternatively, separation can be performed by collecting the Phosphomolecule-phosphoaffinity material complex, or a portion thereof, using a binding partner such as an antibody, ligand, receptor, antigen, complementary sequence, and the like, which selectively binds to an epitope within the phosphomolecule-phosphoaffinity material complex.

Methods described herein can involve detecting formation of a phosphomolecule-phosphoaffinity material complex in order to detect the presence of the phosphomolecule in a sample. Procedures for detecting interaction between molecular entities are well known to those skilled in the art. Such detection procedures generally involve detecting a physicochemical change in at least one of the interacting entities, or detecting the presence of one of the interaction entities when the presence of the other entity is known. A phosphomolecule-phosphoaffinity material complex or portion thereof can be detected by observing a physiochemical property as well as by observing a functional activity. A physicochemical property such as mass, fluorescence absorption, emission, energy transfer, polarization, anisotropy, and the like, can be observed without chemical modification of the phosphomolecule-phosphoaffinity material complex, if desired. Alternatively, the complex or a portion thereof can be subjected to some type of chemical modification that facilitates detection of a physicochemical property. A functional property such as interaction capability, enzymatic activity and the like can be observed by contacting the phosphomolecule-phosphoaffinity material complex or portion thereof, with an appropriate binding partner, for example an antibody, antigen, receptor, ligand, co-factor, subunit, complementary sequence, substrate and the like.

Exemplary well known methods for detecting molecular complexes and components thereof include measurements of absorbance, transmission, mass, charge to mass ratio, fluorescence intensity, fluorescence polarization, time-resolved fluorescence, resonance light scattering, surface-enhanced Raman scattering, electron paramagnetic resonance, refractive index absorbance, nuclear magnetic resonance, microcalorimetry, surface plasmon resonance, refractive index changes, spectropolarimetry, ellipsometry and a variety of spectroscopic characteristics such as those measurable by inductively-coupled plasma mass spectrometry, Fourier transform infrared spectrometry, and atomic absorption spectrometry.

When a phosphomolecule-phosphoaffinity material complex, or component thereof, contains a luminescent or dye component, detection can be by visual observation on a UV transilluminator, or by using a UV-based charged coupled device (CCD) camera detection system, a laser-based gel scanner, a xenon-arc-based CCD camera detection system, a Polaroid camera combined with a UV-transilluminator as well as a variety of other devices used for detecting luminescence.

A phosphoaffinity material useful as a detection agent can have a variety of physical forms. For example, when in particle form, the phosphoaffinity material can be bound to the phosphomolecule and detection can be achieved by detecting a physiocochemical property of the particle or the interaction of the particle with a phosphomolecule. Examples 10 and 13 describe detecting a hydrated metal oxide portion of a phosphomolecule-phosphoaffinity material complex using fluorescent tagging of the hydrated metal oxide. Example 11 describes detecting interaction between a phosphomolecule and a phosphoaffinity material during formation of a phosphomolecule-phosphoaffinity material complex by fluorescence resonance energy transfer. Example 12 describes detecting a metal portion of a phosphomolecule-phosphoaffinity material complex using inductively coupled mass spectrometry.

As a further non-limiting example of a method for detecting a phosphomolecule-phosphoaffinity material complex, binding of hydrated metal oxide particles to phosphorylated substrates on solid supports can be detected by methods similar to those employed in the detection of silver and gold particles by Resonance light scattering (RLS) techniques. RLS particles have been used as labels for analyte detection (Ygueyabide and Ygueyabide, 2001). RLS particles are ultrasensitive labels that have been implemented in a wide range of analytical bioassays. Spherical gold and silver RLS particles of uniform dimension ranging between approximately 40 and 120 nm diameter generate intense monochromatic scattered light when illuminated with a narrow beam of white light. The scattered light signal generated by a single RLS particle is roughly $10^4$ to $10^6$ times greater than the signal obtained for a conventional small molecule fluorophore and relatively easily detected by dark field illumination. The intensity and color of the scattered light generated by individual RLS particles is photostable and dependent upon the particle's composition and diameter. The surface of RLS particles can be derivatized with a variety of functionalities to induce selective binding in analytical assays. Sensitive RLS reagent and instrumentation systems for microarrays, immunocytology/histology, in situ hybridization, microtiter well assays and microfluidics have been developed. Particles made of materials other than cold and silver can be used for an RLS technique if desired. For example, polystyrene-polyacrylic acid particles have been employed in RSL experiments with proteins (Wang et al, 2004). A hydrated metal oxide particle or phosphoaffinity particle including a surface of hydrated metal oxide can be used with RLS assays to detect a phosphomolecule or phosphomolecule-phosphoaffinity material complex.

Other properties of hydrated metal oxide particles can be useful for detecting phosphomolecules and phosphomolecule-phosphoaffinity material complexes. Biosensors, also known as label-less detection systems because of their direct detection of binding without fluorescent or other radioactive labels, detect mass of entities bound to recognition molecules immobilized on a solid support. Some biosensor methods, such as resonant cantilevers, surface acoustic wave sensors and the like, detect mass binding directly. The density of titanium dioxide is about 4 grams per cubic centimeter, significantly higher than that of protein, making it a suitable mass label for this type of sensing. Other sensors, known as optical biosensors, detect changes in refractive index in a local binding area of the sensor. The local refractive index increases as the density of higher index molecules and particles bind to the surface. For example, titanium dioxide exists in two common crystalline forms, anatase with a refractive index of 2.49 and rutile with a refractive index of 2.903, compared to a refractive index of about 1.45 for protein and 1.33 for aqueous buffer. Titanium dioxide therefore can be a sensitive label for optical biosensors. Common optical biosensors include surface plasmon resonance (SPR), evanescent waveguide and colorimetric resonant reflective devices. Finally, surface-enhanced Raman scattering can be useful for ultrasensitive detection, including single-molecule detection. Crystals of Ag—$TiO_2$, for example, can be useful for detecting phosphomolecules and phosphomolecule-phosphoaffinity material complexes by surface-enhanced Raman scattering.

For use as a detection agent, a phosphoaffinity material can be labeled or associated with a detectable tag. For example, a hydrated metal oxide can be labeled with a dye before or after formation of the phosphomolecule-phosphoaffinity material complex. As a specific example, when a metal oxide particle, such as a nanoparticle, is used as the phosphoaffinity material, the nanoparticles can be allowed to bind to a phosphomolecule and can then be labeled with a dye. This can be accomplished, for example, by generating a mordant dye lake (Kornblum and Lopez, 1970). A lake is the water insoluble form of a dye (Marshall and Horobin, 1973; Wou and Mulley, 1988; Lillie et al, 1976; Meloan et al, 1973; Ishikawa et al, 2003). Strong attractive forces between hydrated metal oxides or freshly precipitated salts (such as calcium sulfate or barium sulfate) and certain dye molecules are thought to result in their co-precipitation. Lakes are generally more stable than dyes and are considered ideal for coloring products containing fats and oils or items lacking sufficient moisture to dissolve dyes. A range of dyes representing diverse structural classes can be suitable for highlighting inorganic metal oxide particles in this way, including anthracene, azo, indigoid, diaryl methane, triaryl methane, oxyketone, acridine, azine, oxazine, thiazine, quinoline, polymethine, hydrazone, triazene, porphyrin, porphyazin, quinacridones, formazane nitro, sulfur, nitroso quinone imide, azaphilone, cyanine and azomethine. Non-limiting examples of specific dyes include rhodamine B, rhodamine 6G, acid alizarin violet, morin, tetrahydroxyflavanol, 2-(4-pyridyl)-5-((4-(2-dimethylaminoethylaminocarbamoyl) methoxy)phenyl)oxazole, 2-hydroxyterephthalate, 2-[6-(4'-hydroxy)phenoxy-3H-xanthen-3-on-9-yl]benzoic acid, 2-[6-(4'-amino)phenoxy-3H-xanthen-3-on-9-yl]benzoic acid, N-tert-butyl-phenylnitrone, 2-methyl-2-nitrosopropane-dimer, TEMPO-9-AC, proxyl fluorescamine and coumarin-3-carboxylic acid. Dye families included those listed above are described, for example, in Handbook of Fluorescent Probes and Research Products, Ninth Edition by Dr. Richard P. Haugland (Molecular Probes, 2003).

Certain particles of metal oxides, such as titanium dioxide, are capable of photocatalytic oxidation of dyes (Marci et al, 2003; Saquib and Muneeer, 2003). Photocatalysts, such as Degussa P25 and UV100 are known to facilitate this reaction. A photocatalytic oxidation reaction can be used for detecting a phosphorylated molecule. Since primarily hydroxy derivatives of organic compounds are identified in aqueous suspensions of titanium dioxide that have been irradiated with UV light, the mechanism of degradation is thought to be based upon hydroxyl radical attack. Fluorophores, such as 2-hydroxyterephthalate, 2-[6-(4'-hydroxy)phenoxy-3H-xanthen-3-on-9-yl]benzoic acid (HPF) and 2-[6-(4'-amino)phenoxy-3H-xanthen-3-on-9-yl]benzoic acid (APF) can be employed to selectively detect the highly reactive oxygen species (hROS) generated, such as hydroxyl radicals. In addition, both N-tert-butyl-phenylnitrone and 2-methyl-2-nitrosopropane dimer form relatively stable free radicals that can be detected by their electron paramagnetic resonance. TEMPO-9-AC and proxyl fluorescamine are two additional fluorogenic probes for detecting hydroxyl radicals. Both of these molecules contain a nitroxide moiety that quenches their fluorescence. However, once TEMPO-9-AC or proxyl fluorescamine encounters a hydroxyl radical or superoxide, its fluorescence is restored and the radical's spin signal is reduced, making these probes useful for detecting radicals either by fluorescence or by electron spin resonance spectroscopy. The succinimidyl ester of coumarin-3-carboxylic acid (SECCA) is another useful fluorogenic reagent for detecting hydroxyl radicals. This amine-reactive reagent which can be coupled to a wide variety of molecules, is converted by hydroxyl radicals to a highly fluorescent 7-hydroxycoumarin adduct. Detection of phosphomolecules by hydroxyl radical formation can be performed on a range of solid or semisolid surfaces, including polymeric membranes, polyacrylamide gels, agarose gels, microarrays or polymeric beads.

The methods of the invention for isolating and/or detecting a phosphomolecule can be carried out in a variety of multiwell plate-based formats, if desired. Such methods are exemplified in FIGS. 1 to 4. FIG. 1 depicts a relatively simple fractionation approach, utilizing hydrated metal oxide particles that are suspended above a porous support, positioned at the bottom of the wells of a multiwell microplate device. In the schematic, a filtration device is shown generically. Three wells of the multiwell plate are depicted in the diagram. One plate suitable for this approach is the Millipore MultiScreen 96-well filtration plate, containing Durapore 0.65 µm membrane. The device includes a separation multiwell structure or plate (1) containing separation plate wells (2), output apertures (3) and porous supports (4). Hydrated metal oxide particles (5) are entrapped on top of the porous supports. The particles serve as the affinity matrix for capturing the phosphorylated molecules. Also depicted in the diagram is a wash receiving multiwell structure or plate (7) including wash receiving plate wells (8). The incubation and binding is illustrated in (A). During the incubation and binding (A), samples suspected of containing phosphorylated molecules are prepared in binding buffer (6) and then incubated in the wells of the separation multiwell structure or plate (1). Subsequently, the multiwell device is positioned on a vacuum manifold and samples are filtered (8-18" Hg pressure) to remove any unbound material. The washing is illustrated in (B). A wash buffer (9), typically the binding buffer, is applied to the wells of the microplate device (1) and subsequently filtered through the filtration device using a vacuum manifold. The wash product (10) is collected in the receiving multiwell structure or plate (7). The process of washing can be performed iteratively, as indicated by the curved arrows linking diagram (A) to diagram (B). That is, the wells can be refilled with fresh binding buffer and the particles are washed one or more times to reduce contaminants. The elution is depicted in (C). An elution buffer (11) is applied to the wells of the separation multiwell structure or plate (1), resulting in the release of the phosphorylated molecules from the hydrated metal oxide-coated particles. Finally, the eluent with phosphorylated molecules (12) is collected by vacuum into the eluent receiving multiwell structure or plate (13). The final product is depicted in (D). The eluent receiving multiwell structure or plate (13) now has the eluent containing the phosphorylated molecules (12). This material can be used, either directly or after further processing and sample cleanup, for a variety of downstream assays, including protein or peptide characterization and identification procedures. Alternatively, the phosphorylated molecules can be eluted directly into resin designed to desalt samples, such as pipette tips or multiwell plates filled with reverse-phase packing (Millipore Zip-Tip C18 resin) or anion-exchange packing. For certain downstream applications, elution can not be preferable and assays can be performed directly on the hydrated metal oxide particles themselves.

Figure 2:
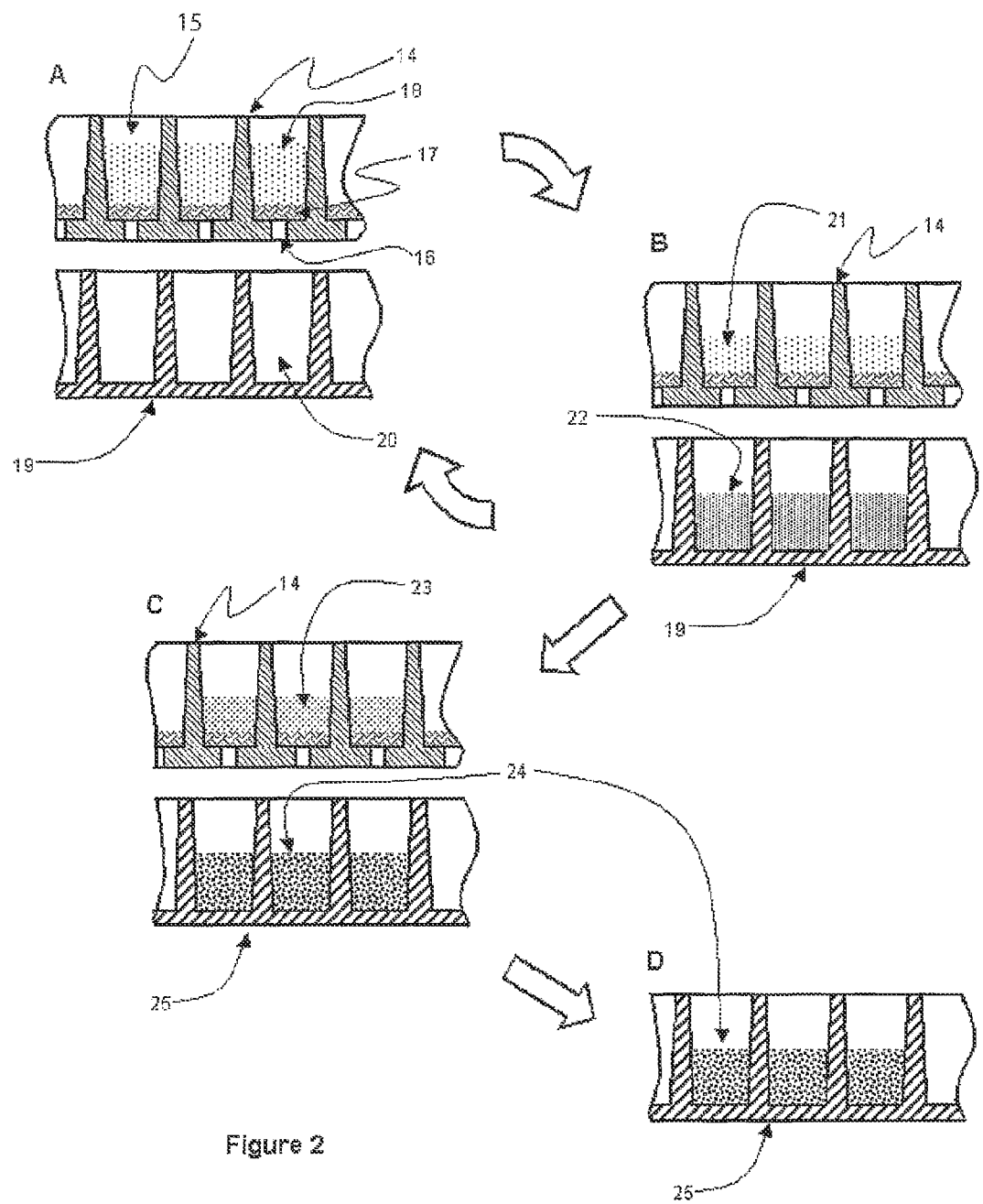
FIG. 2 shows an exemplary process for isolating phosphorylated molecules using hydrated metal oxide/cellulose composite membranes in a multiwell microplate filtration format.

FIG. 2 depicts a more advanced fractionation device, including composite membranes with cellulose or polyvinylidene difluoride core and hydrated metal oxide surface coating. In the schematic, a filtration device is shown generically. Three wells of the multiwell plate are depicted in the diagram. The device includes a separation multiwell structure or plate (14) containing separation plate wells (15), output apertures (16) and hydrated metal oxide-cellulose composite membrane (17). The composite membrane serves as the affinity matrix for capturing the phosphorylated molecules. A single membrane or stacks of membranes can be incorporated into the multiwell structure or plate. Also depicted in the diagram is a wash receiving multiwell structure or plate (19) that includes wash receiving plate wells (20). The incubation and binding is illustrated in (A). During the incubation and binding (A), samples suspected of containing phosphorylated molecules are prepared in binding buffer (18) and then incubated in the wells of the separation multiwell structure or plate (14). Subsequently, the multiwell device is positioned on a vacuum manifold and samples are filtered (8-18" Hg pressure) to remove any unbound material. The washing is illustrated in (B). A wash buffer (21), typically the binding buffer, is applied to the wells of the separation multiwell structure or plate (14) and subsequently filtered through the filtration device using a vacuum manifold. The wash product (22) is collected in the receiving multiwell structure or plate (19). The process of washing can be performed iteratively, as indicated by the curved arrows linking diagram (A) to diagram (B). That is, the wells can be refilled with fresh binding buffer and the composite membranes washed one or more times to reduce contaminants. The elution is depicted in (C). An elution buffer (23) is applied to the wells of the separation multiwell structure or plate (14), resulting in the release of the phosphorylated molecules from the hydrated metal oxide-coated particles. Finally, the eluent with phosphorylated molecules (24) is collected by vacuum into the eluent receiving multiwell structure or plate (25). The final product is depicted in (D). The eluent receiving multiwell structure or plate (25) now has the eluent containing the phosphorylated molecules (24). This material can be used, either directly or after further processing and sample cleanup, for a variety of downstream assays, including protein or peptide characterization and identification procedures. Alternatively, the phosphorylated molecules can be eluted directly into resin designed to desalt samples, such as pipette tips or multiwell plates filled with reverse-phase packing (Millipore Zip-Tip C18 resin) or anion-exchange packing. For certain downstream applications, elution can not be preferable and assays can be performed directly on the composite membranes themselves.

Figure 3:
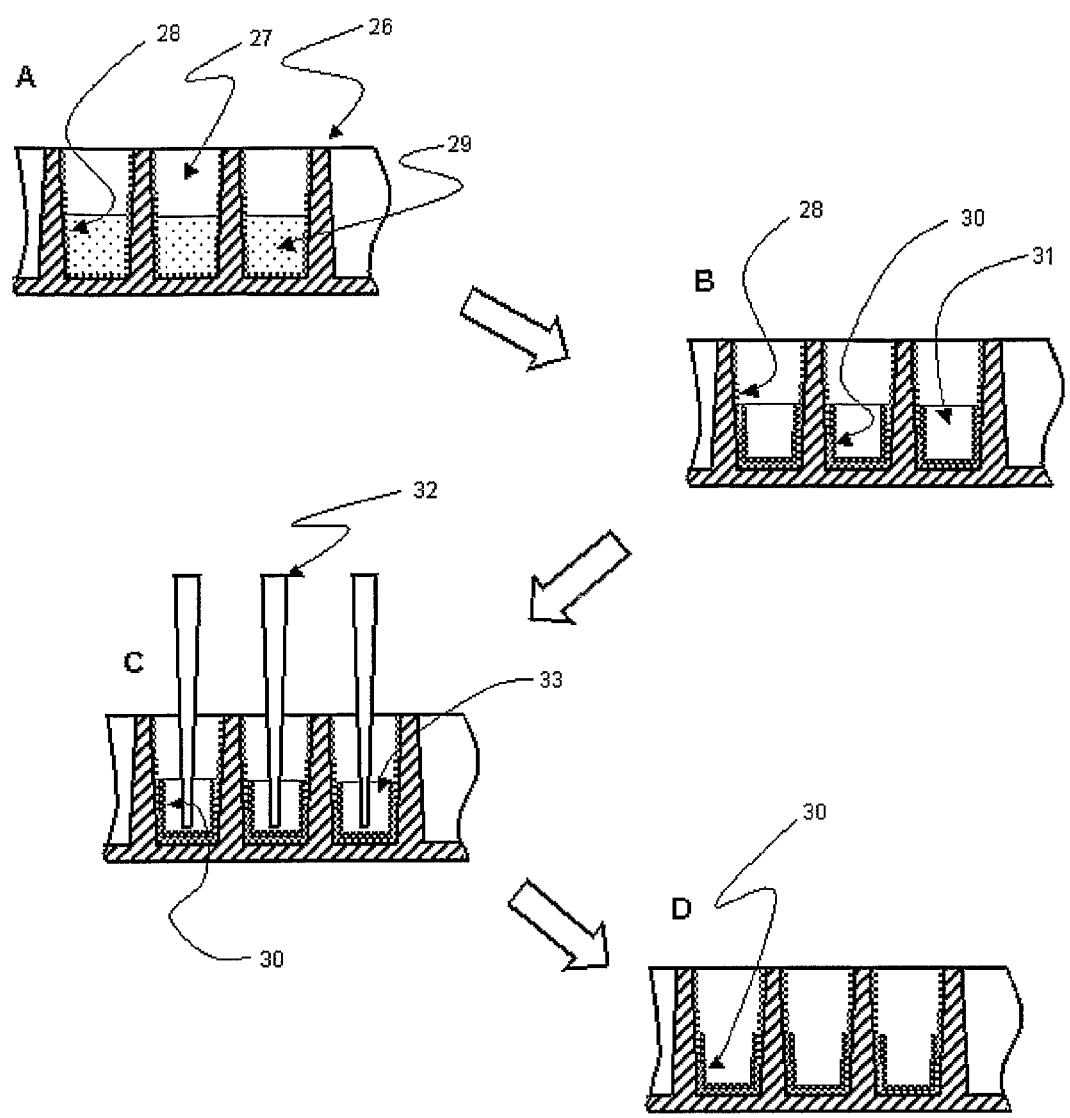
FIG. 3 shows an exemplary process for isolating phosphorylated molecules using a hydrated metal oxide surface on wells in a multiwell microplate filtration format.

FIG. 3 depicts an alternative approach to retrieving phosphorylated molecules using polystyrene multiwell microplates in which the wells of the device have been coated with hydrated metal oxides. In the schematic, a multiwell microplate device is shown generically. Three wells of the multiwell plate are depicted in the diagram. The device includes a separation multiwell structure or plate with hydrated metal oxide coating on the well walls (26) containing separation plate wells (27). The hydrated metal oxide coating (28) serves as the affinity matrix for capturing the phosphorylated molecules. The incubation is illustrated in (A). During the incubation (A), samples suspected of containing phosphorylated molecules are prepared in binding buffer (29) and then incubated in the wells of the separation multiwell structure or plate (26). The binding is depicted in (B). Captured phosphorylated molecules (30) are bound to the hydrated metal coating (28), leaving the sample binding buffer depleted of phosphorylated molecules (31). The washing is depicted in (C). The sample buffer depleted of phosphorylated molecules is removed using a manual or automated pipetting device (32) and wash solution (33), typically the binding buffer, is added back to the wells. This washing can be repeated one or more times. The final product, bound to the walls of the separation multiwell structure or plate with hydrated metal oxide coating is depicted in (D). The phosphorylated molecules (30) are retained on the walls of the wells for subsequent assay, though an elution buffer can be applied, resulting in the release of the phosphorylated molecules from the walls, and then the phosphorylated molecules can be recovered by manual or automated pipetting.

Figure 4:
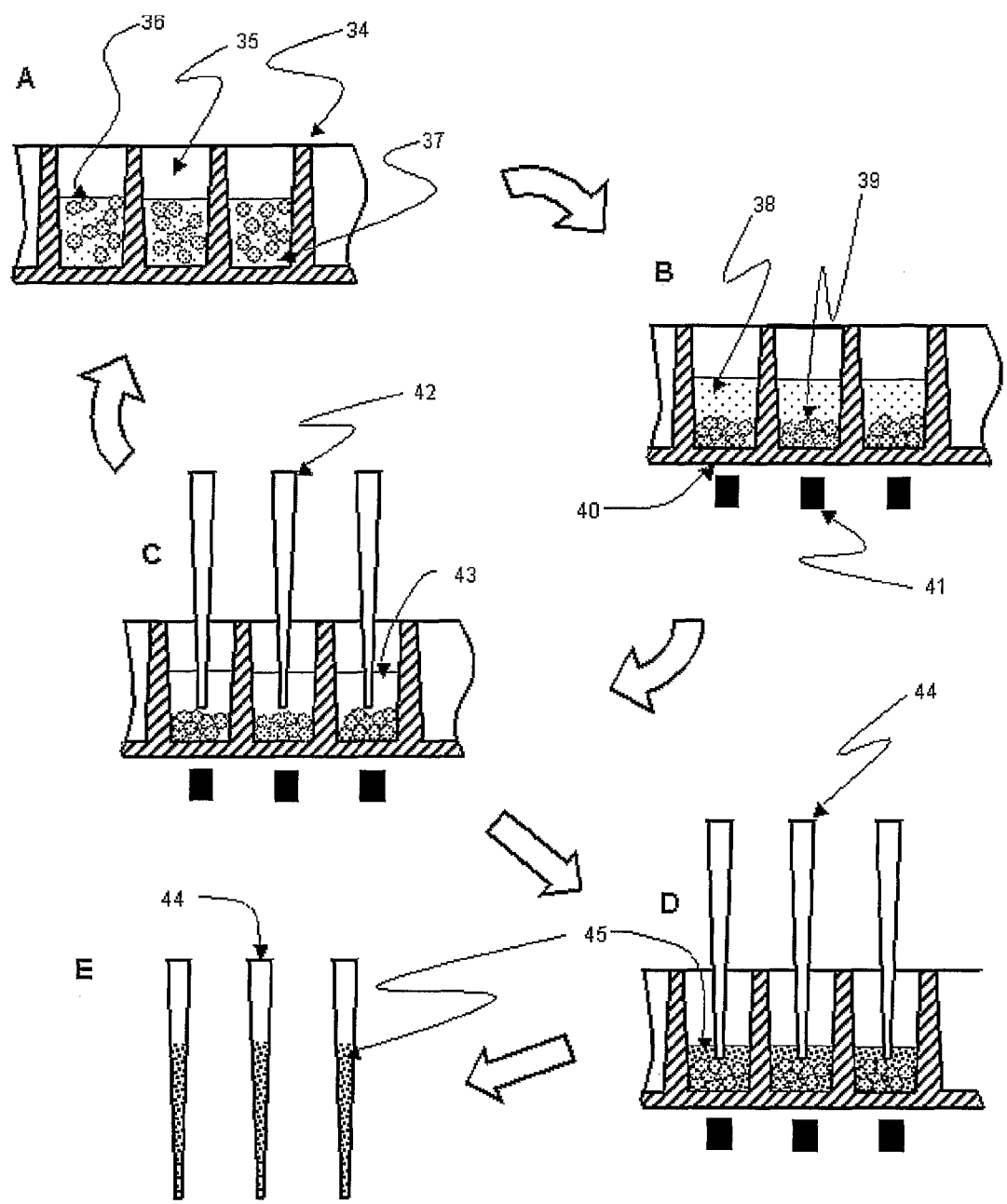
FIG. 4 shows an exemplary process for isolating phosphorylated molecules using magnetic particles coated with a hydrated metal oxide in a multiwell microplate filtration format.

FIG. 4 depicts another approach to retrieving phosphorylated molecules using multiwell microplates and inorganic composite materials. In this instance, particles with a magnetic core and hydrated metal oxide shell are employed. In the schematic, a multiwell microplate device is shown generically. Three wells of the multiwell plate are depicted in the diagram. The device includes a separation multiwell structure or plate (34) containing separation plate wells (35), and magnetic particles with hydrated metal oxide-coating (36). The composite particle serves as the affinity matrix for capturing the phosphorylated molecules. The incubation and binding is illustrated in (A). During the incubation and binding (A), samples suspected of containing phosphorylated molecules are prepared in binding buffer (37) and then incubated in the wells of the separation multiwell structure or plate (34). The binding of the phosphorylated molecules to the magnetic particles and subsequent separation of the particles from the bulk solution with a magnetic separator is shown in (B). The magnetic particles with captured phosphorylated molecules (39) are concentrated at the bottom of the wells (40) with the aid of a magnetic separator (41). In the process the binding buffer (38) is depleted of phosphorylated molecules. The washing is depicted in (C). The sample buffer depleted of phosphorylated molecules is removed using a manual or automated pipetting device (42) and wash solution (43), typically the binding buffer, is added back to the wells. This washing can be repeated one or more times. The elution is depicted in (D). An elution buffer (45) is applied to the wells of the separation multiwell structure or plate using a manual or automated pipette (44), resulting in the release of the phosphorylated molecules from the magnetic particles. The collection of the final product is depicted in (D). The eluted phosphorylated molecules in solution (45) have been drawn up using a manual or automated pipette (44) and can subsequently be dispensed for a variety of downstream assays, including those devised to characterize or identify the phosphorylated molecules. The phosphorylated molecules can be dispensed directly into resin designed to desalt samples, such as pipette tips or multiwell plates filled with reverse-phase packing (Millipore Zip-Tip C18 resin) or anion-exchange packing. If desired, elution need not be performed when assays can be performed directly in a multiwell microplate.

As is described above, a method of the invention can involve filtering a sample in the presence of a phosphoaffinity material, such as particles or membranes. The viscosity of aqueous-based suspensions of particles can change by several orders of magnitude as a function of solution pH. For example, solutions containing 30% anatase have the viscosity of water far from the particle isoelectric point, and the viscosity of molasses near the isoelectric point. When applying samples containing detergents or surfactants to filtration devices, sample foaming can occur during filtration. Such foaming can cause sample handling problems and contribute to cross-contamination among sample wells. Foaming can be reduced by placing samples in solutions containing anti-foaming agents, such as organic solvents, for example methanol or acetonitrile. An exemplary sample solution includes 60% methanol or acetonitrile, 40% water containing 0.1% formic acid or 60% methanol or acetonitrile, 40% 50 mM ammonium carbonate, pH 8.0. Choice of sample solution can take into consideration the isoelectric point of the particular hydrated metal oxide of a selected phosphoaffinity material. The final protein concentration in the sample solution can typically be 0.05-5 mg/ml, such as about 0.4-0.6 mg/ml, although higher or lower protein concentrations can be used. Extraction and solubilization of samples can be facilitated by intermittent vortexing and sonication, if desired. When selecting a solubilization material for use in a method described herein, the interaction of the solubilization material with a selected analytical method can be taken into consideration. For example, surfactants can reduce peptide ionization in mass spectrometry and interfere with chromatographic separations such as reversed-phase liquid chromatography, while solutions containing organic solvents can be more compatible mass spectrometry and liquid chromatography. A buffered organic solvent can be useful for solubilizing and isolating a variety of proteins, including integral membrane proteins, such as proteins containing transmembrane-spanning helices.

The invention provides commercial packages useful for carrying out a method for isolating and/or detecting a phosphomolecule as described herein. A commercial package of the invention contains a phosphoaffinity material incorporating a metal oxide, or reagents useful for forming such a material. A commercial package of the invention can contain a variety of components in addition to a phosphoaffinity material. A package can contain, for example, instructions for preparing a phosphoaffinity material; for using a phosphoaffinity material for isolating a phosphomolecule; for using a phosphoaffinity material to detect a phosphomolecule, or a combination of instructions. Instructions optionally can include a recommendation regarding the concentration of sample for use in a particular application, as well as guidance regarding temperature, buffer conditions and incubation time periods. A commercial package of the invention optionally can contain other components, such as one or more protein or peptide fractionation devices, labeled polypeptides, fluorescent dyes, binding buffers, wash buffers, molecular weight standards, isoelectric point standards, phosphorylation standards, fixatives, stains, antibodies, lectins, aptamers, phosphatase substrates, kinase substrates, detection reagents, magnetic separator, and the like. Those skilled in the art will be able to select suitable components for inclusion in a commercial package of the invention based on such exemplary factors as design of the assay protocol, the particular phosphoaffinity material used for detection or isolation, method of measurement to be employed once the assay has been performed, consumer price point, shipping and handling suitability and the like.

In particular embodiments, the phosphoaffinity material includes a support. Exemplary supports include membranes, particles, matrices, spin-columns, microcolumn pipette tips, multi-well microwell strips, and multi-well microplates. Specific examples of phosphoaffinity materials include filtration devices including membranes and filters containing one or more porous or semi-porous hydrated metal oxide surfaces and/or coatings; filtration devices containing filters, particles and/or membranes that contain or incorporate hydrated metal oxides as a coating on fiber surfaces, entrapped within the membrane's polymeric matrix or pores or presented as a layer on top of the membrane; and filtration devices configured as spin columns, microcolumn pipette tips, multi-well strips, and/or multi-well microplates.

The invention provides a variety of commercial packages useful for carrying out a method for isolating and/or detecting a phosphomolecule in a sample. In an embodiment, a commercial package includes a hydrated metal oxide attached to a support, wherein the hydrated metal oxide comprises yttrium. In another embodiment, a commercial package includes a phosphoaffinity unit, the unit comprising a plurality of support sheets coated with a hydrated metal oxide. As used herein, the term "phosphoaffinity unit" means a device that contains a phosphoaffinity material, such as a sample receptacle, column, plate and the like. The support sheet can be, for example, a membrane or paper, such as cellulose. In a further embodiment, a commercial package contains a phosphoaffinity particle comprising a hydrated metal oxide and a detectable agent that binds to the hydrated metal oxide. In an embodiment, a commercial package of the invention includes a phosphoaffinity material comprising titanium dioxide particles, and a detectable agent that binds to titanium dioxide particles. In a specific embodiment, the titanium dioxide particles are crystals of titanium dioxide. In another embodiment, the titanium dioxide particles are a particle support coated with titanium dioxide.

The invention provides a composition comprising a complex of a phosphoaffinity material and a phosphomolecule. The complex can be used, for example, as a standard, control, binding partner for a known or unknown substrate or analyte, and the like.

It is understood that modifications that do not substantially affect the activity of the various embodiments of this invention are also included within the definition of the invention provided herein. Accordingly, the following examples are intended to illustrate but not limit the present invention.

EXAMPLE 1

This example describes isolation of phosphoproteins by selective binding with yttrium oxide, yttrium iron garnet or titanium dioxide.

Affinity columns for isolating phosphopeptides were prepared as follows: 15-25 mg of yttrium oxide (Aldrich catalog #205168-10), yttrium iron garnet (Aldrich catalog #634417-10) or titanium dioxide (Aldrich catalog #634662-25) particles was packed into five inch disposable columns (Evergreen Scientific, Los Angeles, Calif.). Each column was washed with 2×1 ml of 1% (v/v) formic acid in deionized water. The contents of the columns were mixed intermittently using a vortex mixer. Each column was then washed with 3×1 ml of binding buffer (0.5 M sodium acetate, 0.2 M sodium chloride pH 5.5). The contents of the columns were mixed intermittently using a vortex mixer.

Phosphoproteins were isolated as follows: one ml of a solution (0.2 μg/μl, total protein) containing both bovine carbonic anhydrase II and chicken ovalbumin (~1:1 ratio) in binding buffer was added to each column. The suspension was intermittently mixed for one minute using a vortex mixer. The columns were capped on both ends and the particle suspension was allowed to incubate in a horizontal position for one hour with agitation, using a Nutator mixer. The columns were placed in a vertical position, drained and packed, and the hydrated metal oxide particle beds were rinsed with 3 volumes of 0.5 ml binding buffer. The columns were then washed with 3 volumes of 0.3 ml elution buffer (phosphate-buffered saline, pH 7.4). The first elution wash was equilibrated in the column for one hour before draining. The combined eluents were collected in a 15 ml centrifuge tube. Proteins present in the elution buffer were precipitated by addition of ice cold acetone to a total volume of 12 ml, vortex mixing and centrifuging for five minutes. The acetone was removed and the resulting white solid was dissolved in 20 μl of 10 mM Tris HCl, 2% (v/v) SDS, pH 7.6 prepared in deionized water and 30 μl of sample dilution buffer. The sample dilution buffer was prepared by combining 0.1 ml of 0.5 M dithiothreitol in ethanol, 0.9 ml of 10 mM Tris HCl, 2% (v/v) SDS, pH 7.6 in deionized water and 1 ml of NuPage LDS sample buffer 4× (Invitrogen Corporation, Carlsbad, Calif.). One ml of bovine carbonic anhydrase/chicken ovalbumin control protein sample (~1:1) (0.2 μg/μl total protein) in binding buffer was also acetone precipitated directly to serve as a reference standard for monitoring the enrichment of the phosphorylated protein (ovalbumin) relative to the unphosphorylated protein (carbonic anhydrase).

Protein samples were analyzed by SDS-polyacrylamide gel electrophoresis, according to standard procedures. Bio-Rad Broad Range molecular weight markers were included in some lanes on the gels to facilitate identification of serum albumin and ovalbumin based on molecular weight. After electrophoresis, the gels were fixed, stained with SYPRO Ruby protein gel stain (Molecular Probes/Invitrogen, Eugene, Oreg.), destained and fluorescent signal imaged using the ProXPRESS 2D proteomic imaging system (PerkinElmer LAS, Boston, Mass.).

Figure 5:
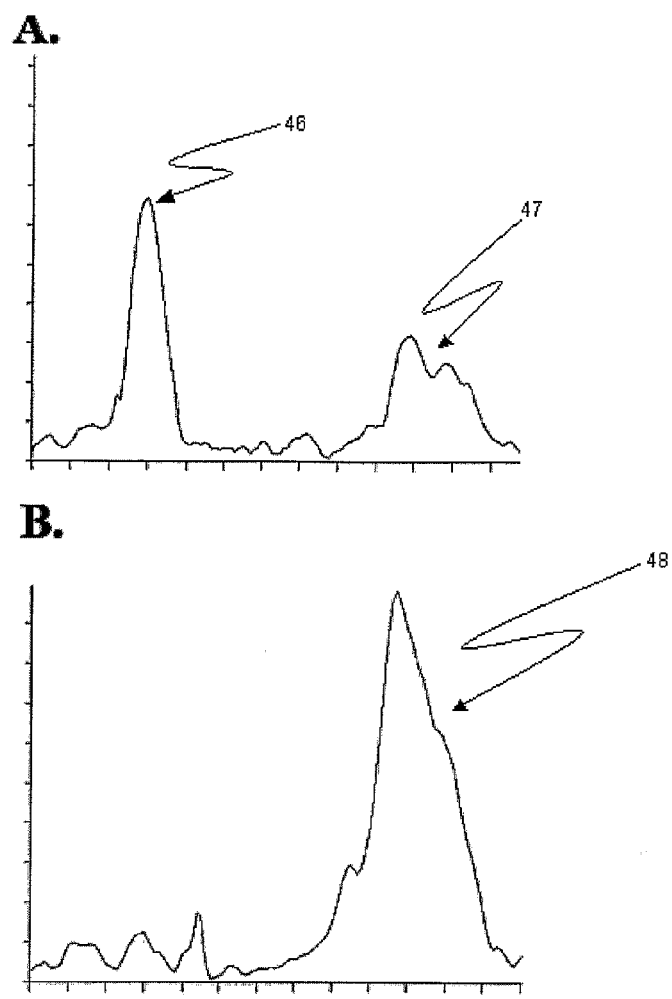
FIG. 5 shows selective isolation of phosphorylated proteins using an yttrium oxide phosphoaffinity material.
Figure 6:
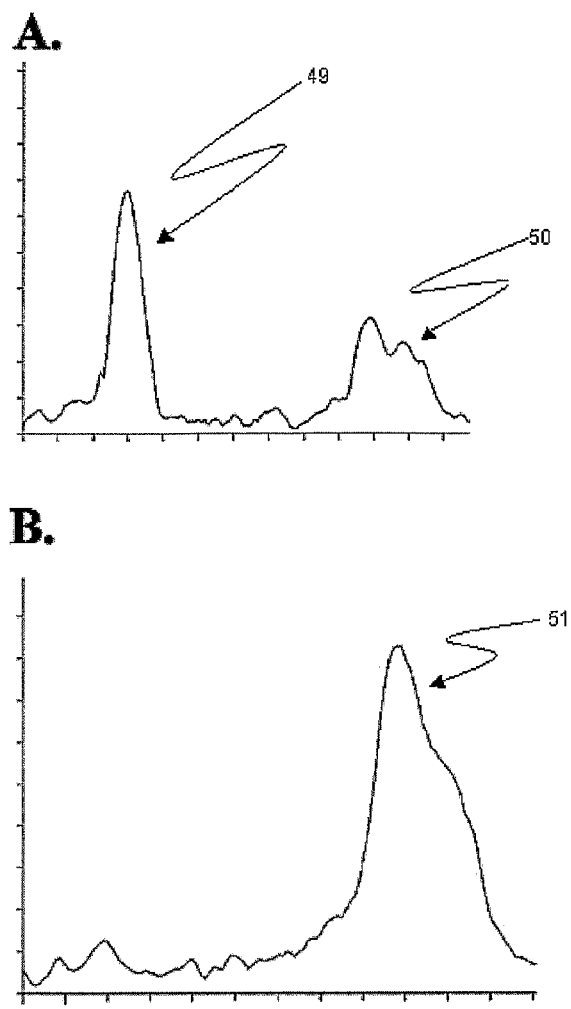
FIG. 6 shows selective isolation of phosphorylated peptides using an yttrium iron garnet oxide phosphoaffinity material.
Figure 7:
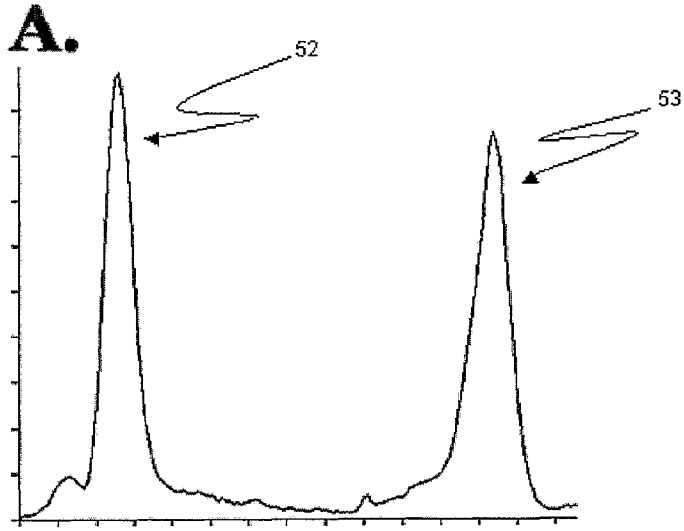
FIG. 7 shows selective isolation of phosphorylated peptides using a titanium dioxide phosphoaffinity material.
Figure 7:
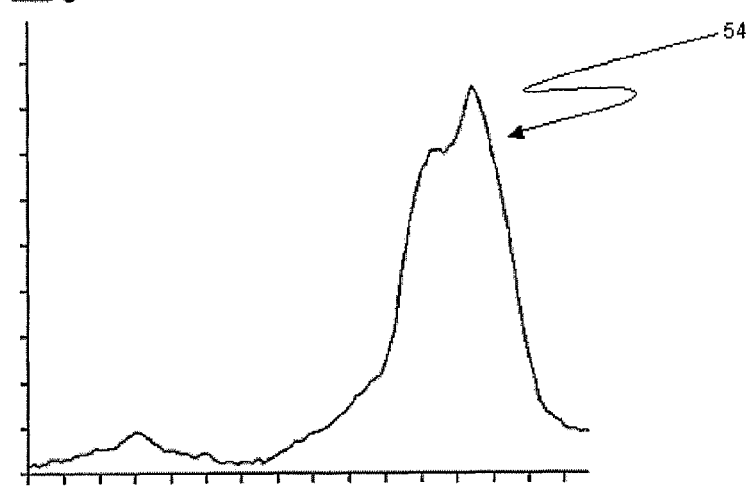

Representative line traces obtained from resultant protein samples processed on yttrium oxide, yttrium iron garnet or titanium dioxide are shown in FIGS. 5 to 7, respectively. The profiles of the reference starting materials are shown in part A of the figures, while the isolated material is depicted in part B of the figures. The X-axis of the figures represents the distance traveled by the proteins in the electrophoresis gel, while the Y-axis corresponds to the fluorescence intensity of the total protein stain.

In FIGS. 5 to 7, peaks identified as (46), (49) and (52) correspond to fluorescently stained carbonic anhydrase bands, while (47), (48), (50), (51), (53) and (54) correspond to fluorescently stained ovalbumin bands. These data show that ovalbumin (the phosphorylated protein) was separated from carbonic anhydrase (the non-phosphorylated protein) using affinity columns prepared with particles of yttrium oxide, yttrium iron garnet and titanium dioxide.

EXAMPLE 2

This example describes isolation of phosphopeptides using a titanium dioxide phosphoaffinity material in a 96-well filtration plate format.

The phosphoaffinity material in 96-well filtration plate format was prepared as follows: about 0.2 g of titanium dioxide particles was activated in 10 ml of 1% formic acid for 10 min at room temperature and washed with deionized water several times using centrifugation to collect the beads. The pre-washed beads were re-suspended in 10 ml of deionized water and 200 μl/well of the resulting suspension was pipetted into the 96-well MULTISCREEN DV (Millipore Corporation, Bedford, Mass.) plate. The resulting titanium dioxide loaded plate was pre-equilibrated by washing wells in 500 mM sodium acetate pH5.5+200 mM NaCl buffer (Binding Buffer).

Isolation of phosphopeptides was performed as follows: about 200 μl/well of the 2.5 μM solution of phosphorylated synthetic peptide and 1 μM of non-phosphorylated synthetic peptide was allowed to bind in wells of the titanium dioxide loaded plate by incubating the particles with peptides on a plate shaker for 15 min at room temperature followed by vacuum-assisted passage of the peptide solution through the titanium dioxide particles. Different starting concentrations for phosphorylated and non-phosphorylated peptide were used to balance the peak intensities for these peptides in MS spectra, as phosphorylated peptides are known to be more difficult to ionize. The material that was unbound to the titanium dioxide particles was collected as a flow-through fraction concentrated on a ZipPlate as recommended by the manufacturer. Remaining unbound or non-selectively bound material was washed off the titanium dioxide particles with ten 180 μl volumes of the Binding Buffer. Peptides bound to the titanium dioxide particles were eluted with 180 μl of 1% ammonium hydroxide solution and concentrated on a Zip-Plate as recommended by the manufacturer. The concentrated peptides were eluted from the ZipPlate directly on to a MALDIChip with the 5 mg/ml α-cyano-4-hydroxycinnamic acid+ 50% acetonitrile+0.1% trifluoroacetic acid solution and analyzed on the prOTOF 2000 mass spectrometer.

Materials used in the above experiments included synthetic p60 c-src peptide (521-533) Thr-Ser-Thr-Glu-Pro-Gln-Tyr-Gln-Pro-Gly-Glu-Asn-Leu-COOH (cat #8249), and pp60 c-src peptide (521-533) Thr-Ser-Thr-Glu-Pro-Gln-Tyr(P)-Gln-Pro-Gly-Glu-Asn-Leu-COOH (cat #8250) were obtained from SynPep Corporation, Dublin, Calif. The "P" is parentheses indicated phosphorylation of the tyrosine residue. Titanium dioxide particles of mesh-325 (cat#248576-100 g), acetonitrile (cat#270717-6X1L), trifluoroacetic acid (cat#302031-100ML), ammonium hydroxide (cat#338818-100 ML), formic acid (cat# PR15225KR), sodium acetate (cat#241245-500G), and sodium chloride (cat#22351-4) were purchased from Sigma-Aldrich (St. Louis, Mo.). Zip-Plates (cat# ZPC180010), 96-well MultiScreen-DV plates (cat# MADVN6510), and custom vacuum manifold were obtained from Millipore Corporation (Billerica, Mass.). Polypropylene 96-well collection plates (cat# EK-21261) were purchased from E & K Scientific Products, Inc. (Los Gatos, Calif.). Alpha-cyano-4-hydroxycinnamic acid (cat# M001) and Peptide calibration Mix 1 (cat# C101) were purchased from LaserBio Labs (Sophia-Antipolis Cedex, France). Mass spectrometry (MS) spectra were acquired using MALDIChip target plates (catalog #N7014021) and a prOTOF 2000 O-TOF mass spectrometer (PerkinElmer/SCIEX, Concord, ON, Canada).

Figure 8:
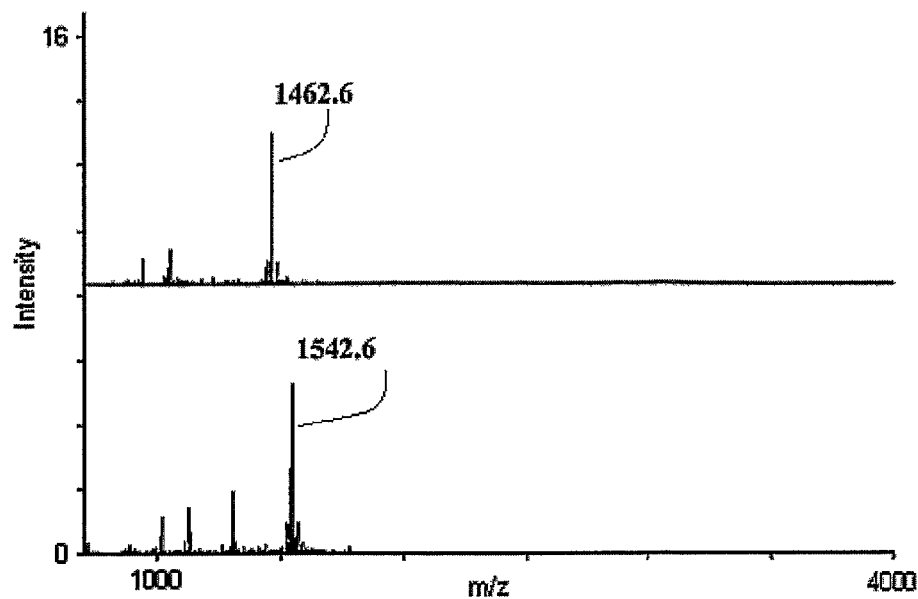
FIG. 8 shows positive control MALDI-TOF mass spectra of starting sample containing p60 c-src peptide (top) and phosphorylated p60 c-src peptide (pp60 c-src peptide) (bottom) spotted directly onto MALDIChip plates.
Figure 9:
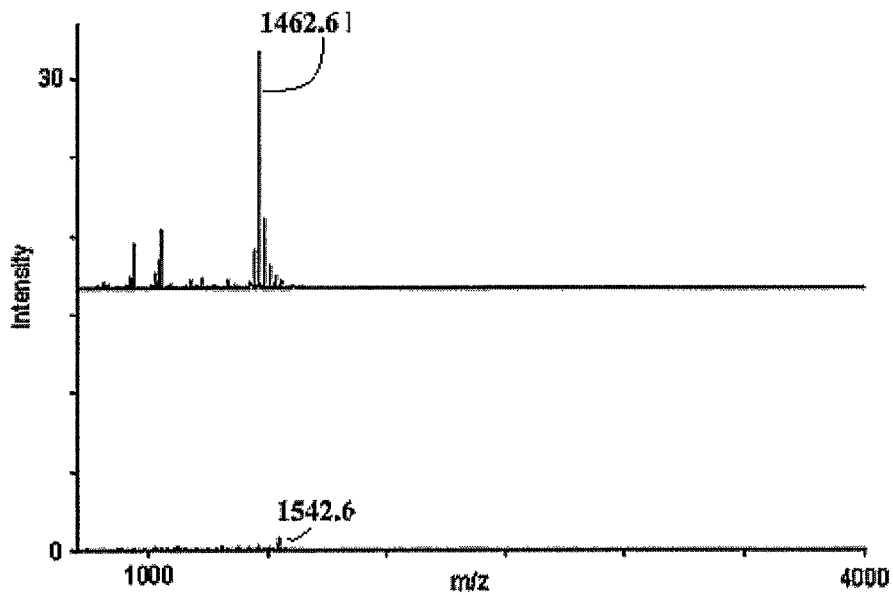
FIG. 9 shows MALDI-TOF mass spectra of a non-phosphorylated peptide fraction that did not bind to titanium dioxide particles (flow-through fraction).

FIG. 8, top and bottom, respectively depict MALDI-TOF mass spectrometry profiles of unphosphorylated c-src peptide (p60 c-src peptide) and phosphorylated c-src peptide (pp60 c-src peptide) spotted directly onto a MALDIChip plate without fractionation. The monoisotopic peak masses corresponding to the expected peptide masses were shown for each MS spectrum. The ratio of intensities between pp60 c-src peptide and p60 c-src peptide peaks was 1.1. FIG. 9 depicts the MALDI-TOF mass spectrometry profile of the peptide fraction that was unbound to the titanium dioxide particles.

Figure 10:
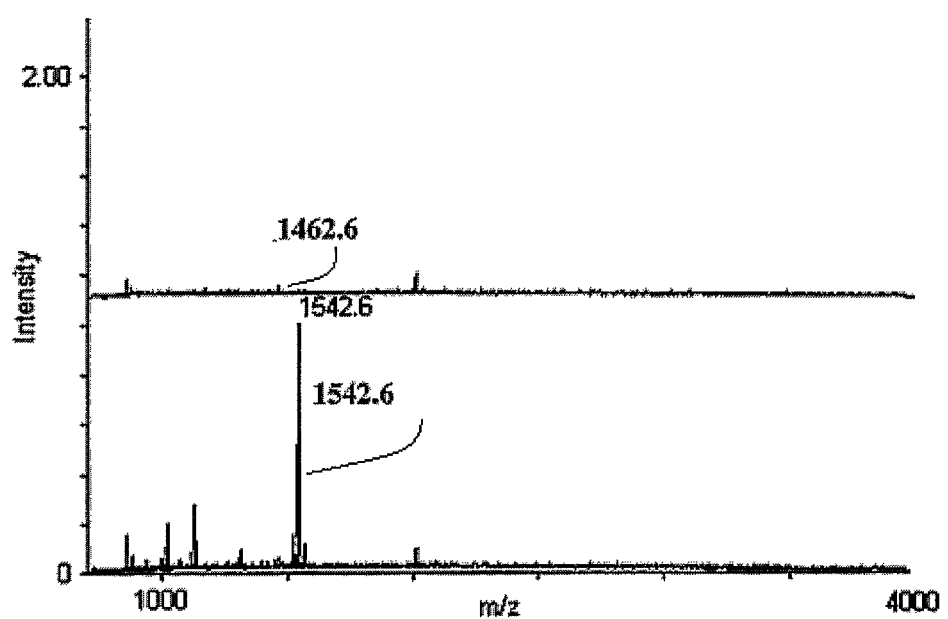
FIG. 10 shows MALDI-TOF mass spectra of a phosphorylated peptide fraction eluted from titanium dioxide particles.

These data show that the pp60 c-src peptide (bottom) was retained on the titanium dioxide particles while the p60 c-src peptide (top) passed through the titanium dioxide particles. The ratio of intensities between pp60 c-src peptide and p60 c-src peptide peaks is 0.05. FIG. 10 depicts the MALDI-TOF mass spectrometry profile of the peptide fraction eluted from the titanium dioxide particles. The pp60 c-src peptide was selectively retained and eluted from the titanium dioxide beads. A scarcely detectable amount of non-phosphorylated peptide was retained on the titanium dioxide particles. The ratio of intensities between pp60 c-src peptide and p60 c-src peptide peaks was 20.

Four independent fractionations and analyses were performed for each peptide. The expected peptide masses for p60 c-src peptide and pp60 c-src peptide are 1463.0 and 1543.5 daltons, respectively, and can be readily distinguished on the corresponding MS spectra (FIGS. 8 to 10). Analysis of unbound and bound peptide fractions obtained from the titanium dioxide particles demonstrates selective retention and recovery of phosphorylated peptides under the described experimental conditions. The ratio of intensities of the directly analyzed unfractionated peptides was close to 1 (FIG. 8), indicating that peptide ionization responses were balanced under the experimental conditions and can be compared to one another. Taken together, these data indicate that about 20-fold more pp60 c-src peptide was retained and eluted on titanium dioxide particles than p60 c-src peptide.

EXAMPLE 3

This example describes isolation of phosphoproteins using a titanium dioxide phosphoaffinity material, further fractionation using gel electrophoresis and detection using mass spectrometry.

A sample enriched for phosphoproteins can be prepared using a titanium dioxide phosphoaffinity material, as is described above in Examples 1 and 2. The sample is then separated on an SDS-polyacrylamide gel using standard methods. Gels are stained using SYPRO Ruby protein gel stain per manufacturer's suggestions and fluorescent signal is imaged using a ProXPRESS 2D proteomic imaging system or similar gel imaging device. The gel is scanned with a 460/80 nm excitation band pass filter and 650/150 nm emission band pass filter. Fluorescent spots are then excised from the gel. For destaining, the spots are placed into a 1.5 mL microcentrifuge tube and destained with 100 μL 50% methanol, 5% acetic acid for 30 min, 100 μL 0.1% trifluoroacetic acid for 30 min, 100 μL 50% methanol/5% acetic acid for 30 min, and finally dehydrated in 100 μL 100% acetonitrile for 10 min. The pieces are air dried before reduction and alkylation. If the proteins have already been reduced and alkylated before the 2-D gel electrophoresis, the following alkylation and reduction steps can be omitted.

For the alkylation and reduction of cysteine residues, enough 20 mM dithiothreitol (DTT) is added to a solution of 0.1 M $NH_4HCO_3$ to completely cover the dried gel pieces (~50 μL). It can be necessary to add more solvent as the gel pieces re-swell. Gel pieces are incubated at 56° C. for 1 hr. The DTT solution is removed and an equal volume (50 μL) of 100 mM iodoacetamide in 50 mM $NH_4HCO_3$ is added. The gel pieces are incubated at room temperature in the dark for 30 min., the supernatant is discarded and the gel pieces are washed twice with 100 μL 0.1 M $NH_4HCO_3$ for 15 min. with occasional vortexing to wash out excess reagents. To extract any excess reagents, the gel pieces are washed with 100 μL of 0.1 M $NH_4HCO_3$/50% ACN for 15 min with occasional shaking. The supernatant is discarded and the gel pieces are washed with 100% acetonitrile. The supernatant is discarded and the gel pieces are thoroughly dried in air.

For in-gel digestion with trypsin, a fresh solution of 0.05 mg/ml modified trypsin in 50 mM $NH_4HCO_3$/10% acetonitrile is prepared. The reagent is kept on ice if not used immediately. 10 μL of the fresh trypsin solution is added and the gel pieces are allowed to soak up the trypsin solution before proceeding to the next step. This typically requires about 10 min. of incubation. The gel pieces are fully re-swelled by adding 20 μL of 50 mM $NH_4HCO_3$/10% acetonitrile (final volume is roughly 30 μL) and incubated overnight at 37° C.

To extract the peptides, proteolytic digestion is terminated by adding 1 μL of 10% trifluoroacetic acid for 10 min. at room temperature. The sample is mixed using a Vortex, mixer, briefly centrifuged and the supernatant is removed by aspiration and then placed in a 0.5 ml micro tube. 50 μL of 0.1% trifluoroacetic acid is added to the gel pieces and incubation is carried out for an additional 30 min. This solution is mixed and spun, and then the resulting supernatant is combined with the first one. 50 μL 60% acetonitrile/0.1% trifluoroacetic acid, is added to the gel pieces and incubated for 30 min. After mixing, spinning, and combining with first supernatant in the tube the combined supernatant mixture is dried in a Speed-Vac vacuum concentrator and dissolved again in 10 μL 10% acetonitrile/0.1% trifluoroacetic acid. The peptide mix is then optionally desalted and concentrated with a C18 ZipTip column from Millipore or spotted directly onto a MALDI-TOF target plate, depending on the sample concentration. The concentrated peptide mixture is mixed with 0.5 μL matrix (5 mg/ml α-cyano-4-hydroxycinnamix acid in 50% acetonitrile, 0.1% trifluoroacetic acid) and 0.5 μL of sample is spotted on the target plate. The spot is allowed to air dry and is then analyzed using a prOTOF 2000 MALDI O-TOF Mass Spectrometer (PerkinElmer, Boston, Mass.) or similar instrument. The protein is subsequently identified based on its characteristic peptide mass profile.

In summary, a phosphoprotein enriched sample prepared using a titanium dioxide phosphoaffinity material can be subjected to further fractionation, such as by gel electrophoresis, prior to analysis by mass spectrometry.

EXAMPLE 4

This example describes preparation of a titanium oxide phosphoaffinity material in membrane format.

Multiwell plates containing membranes coated/impregnated with titanium oxide were prepared as follows: MULTISCREEN 96-well (Millipore Corp., Bedford, Mass.) plates were cleaned by washing 3 times with 250 μl/well of absolute ethanol followed by 5 times wash with 250 μl/well of deionized water (Milli-Q water, Millipore Corp.). Plates were dried at 60° C. for 30 min.

A titanium dioxide coating solution (50 mM Ti fluoride solution) was prepared in deionized water and adjusted to pH ~1.8 by weighing 0.31 g of Ti (IV) fluoride in a clean polycarbonate screw-cap container; adding 20 ml of water, closing the container, and placing it on a magnetic mixer for 60 min to completely dissolve the Ti (IV) fluoride. Very slowly (~1 ml/min), 26 ml of an aqueous solution of 0.1% NH4OH was introduced with constant mixing to avoid localized precipitation of titanium dioxide, to obtain a solution having pH close to pH 1.8. If needed, the pH of the solution can be adjusted by addition of more 0.1% $NH_4OH$. The volume of the Ti (IV) fluoride solution was adjusted to 50 ml final volume by adding deionized water.

The coating solution (250 μl/well) was applied to the wells of a pre-washed and dried MULTISCREEN 96-well plate. The plate was sealed with a self-adhesive cover to prevent evaporation of the solution. The plate was incubated at 60° C. in a convection oven for 2 hours. Titanium dioxide coating solution was removed by gently tapping the plate upside down on a clean absorbing surface, such as a paper towel. The wells were then rinsed with 250 μl of deionized water. The plate was gently tapped upside down on a clean absorbing surface to remove water from the wells. The wash steps were repeated 3 more times. The plates were then dried at 60° C. in a convection oven for 40 minutes. Derivatized plates were stored in a desiccated state until ready for use. Materials used for the above preparation include MULTISCREEN 96-well plates (Cat# MADVN 6510; Millipore Co.); titanium (IV) fluoride (Cat#333239-100 g; Sigma); Lab ware (Cat#353073; Becton Dickinson); and other reagents were purchased from Sigma.

EXAMPLE 5

This example describes isolation of phosphopeptides using a titanium dioxide phosphoaffinity material in membrane format.

Phosphopeptides were enriched from a mixture containing phosphopeptide (P2P) and non-phosphorylated peptide (P2). The peptides were as described in the previous samples, p60 c-src peptide (P2) and pp60 c-src peptide (P2P). For these studies about 16 μl of 100 μM solutions of P2 and P2P in water were mixed together and diluted 1:25 in Binding Buffer (20% acetonitrile+20% isopropanol+0.1% formic acid). One half of the resulting peptide mix solution was split further into 2 wells of the collection plate and set aside as non-fractionated positive controls. The other half of the peptide mix sample was fractionated on titanium dioxide coated MULTISCREEN 96-well plate (as prepared in Example 4) as follows. Equal amounts of the sample were loaded into 2 separate wells. The titanium dioxide plate was placed on top of a collection plate in a vacuum manifold and low vacuum was applied (less than 25 mm of Hg), allowing the peptide solution to pass through the titanium dioxide coated membrane and any unbound material to be collected in the collection plate for analysis. The positive control samples and the unbound material samples were placed into a vacuum oven at 60° C. for about 30 min to evaporate the acetonitrile and isopropanol before concentrating the samples on a C18-based ZipPlate (Millipore, Bedford, Mass.). After evaporation of organic solvents, the concentrated samples were diluted in 0.1% formic acid to the original volume. The samples on titanium dioxide coated membrane were washed using 180 μl, of the Binding Buffer. The washing step was repeated 5 times. The samples were eluted with 300 μl of 100 mM ammonium phosphate pH 8.5, and collected in a collection plate using a vacuum manifold as described above. For these experiments, phosphorylated and non-phosphorylated forms of p60 c-src (521-533) peptide (abbreviated P2 and P2P hereafter, respectively) were obtained from SynPep Corporation, Dublin, Calif. The expected m/z values for P2 and P2P are 1463 Da and 1543 Da, respectively.

The eluted samples were acidified by adding about 30 μl of 10% formic acid. Samples were concentrated on a ZipPlate and eluted directly onto a MALDI Chip (PerkinElmer) in duplicate for analysis on the prOTOF MALDI-TOF mass spectrometer (PerkinElmer/SCIEX).

Figure 11A:
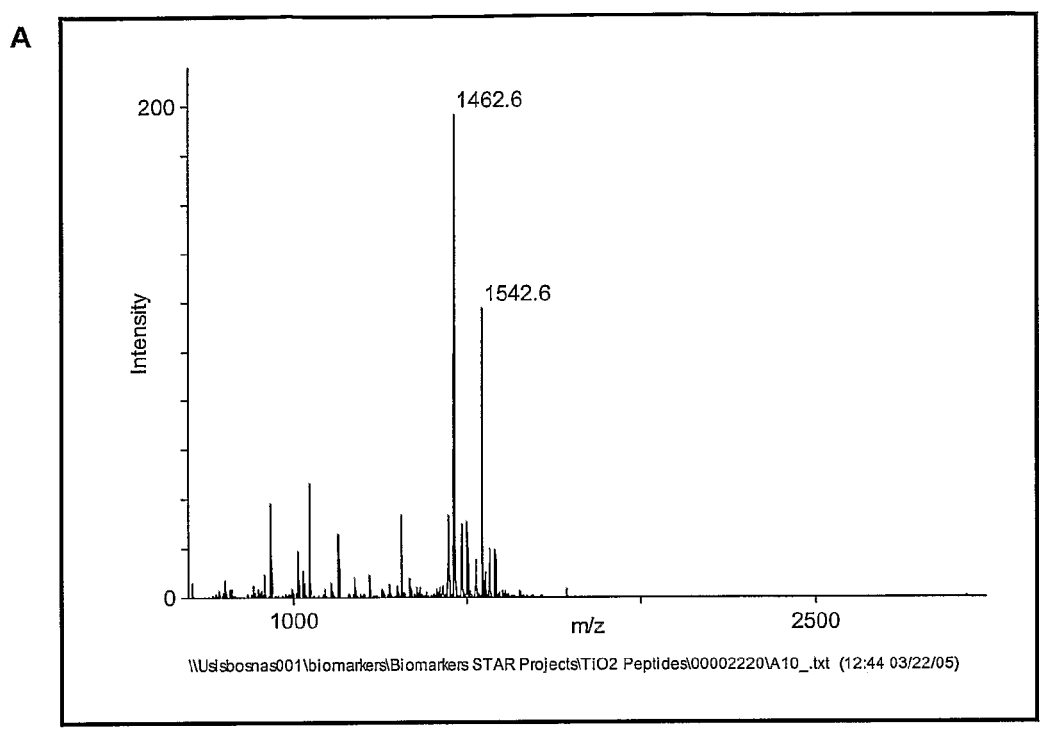
FIG. 11A shows a mass spectrum of starting material phosphorylated (P2P) and non-phosphorylated (P2) peptides.
Figure 11B:
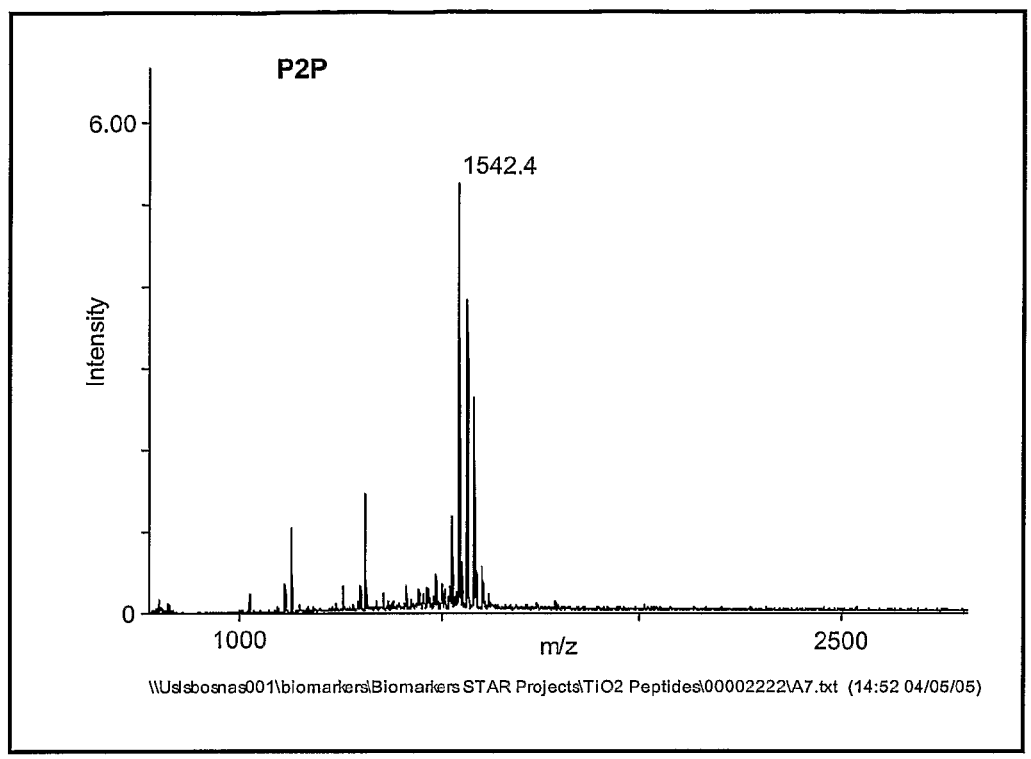
FIG. 11B shows a mass spectrum of peptides that bound to titanium oxide coated membrane.
Figure 11C:
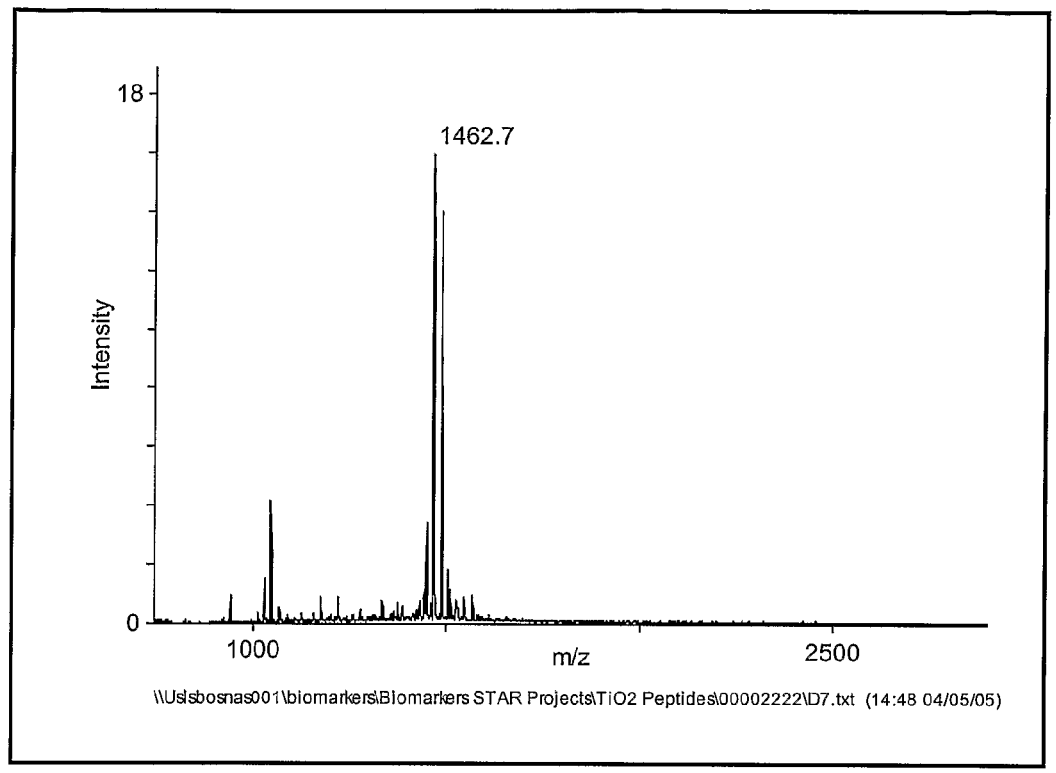
FIG. 11C shows a mass spectrum of peptides that did not appreciably bind to the membrane (flow-through fraction).

The results are represented by mass spectra of the non-fractionated positive control containing P2 and P2P, bound fraction and non-bound fraction are shown in FIG. 11. FIG. 11A shows presence of P2 (1462.6 m/z) and P2P (1542.6 m/z) in the starting mixture. FIG. 11B shows that P2P (1542.6 m/z) bound to the titanium dioxide phosphoaffinity material, while P2 did not. FIG. 11C shows that P2 (1462.7) was present in the unbound fraction. The non-phosphorylated peptide P2 was detected only in the unbound fraction while the phosphorylated peptide P2P was recovered in the eluted fraction. Both peptides can be easily distinguished in the non-fractionated samples based on their respective masses.

In summary, a phosphopeptide containing sample was enriched for phosphopeptide content by processing on a titanium dioxide coated membrane in a filtration format.

EXAMPLE 6

This example describes isolation of phosphopeptides from a complex mixture containing serum, using a titanium dioxide phosphoaffinity material in particulate format.

A complex phosphopeptide mixture was prepared by adding about 400 pmol of phosphorylated (P2P) and non-phosphorylated (P2) synthetic peptides to 20 μl of human serum (Sigma). Unadulterated serum sample was used as a negative control. The two samples are referred to herein as spiked and non-spiked samples, respectively.

Both spiked and non-spiked serum samples were pre-fractionated by adding 2 volumes of acetonitrile resulting in dissociation of protein bound peptides and precipitation of serum proteins. Peptides in solution phase were separated from the precipitated proteins by centrifugation. Pre-fractionated samples were diluted in 0.1% formic acid and isopropanol was added to a final buffer composition matching the Binding Buffer described in Example 5. The samples were processed and analyzed in a similar way as described in Example 5 except that titanium dioxide particles of mesh −325 were deposited on top of Multiscreen membranes and used as chromatographic media instead of titanium dioxide coated membranes.

Figure 12A:
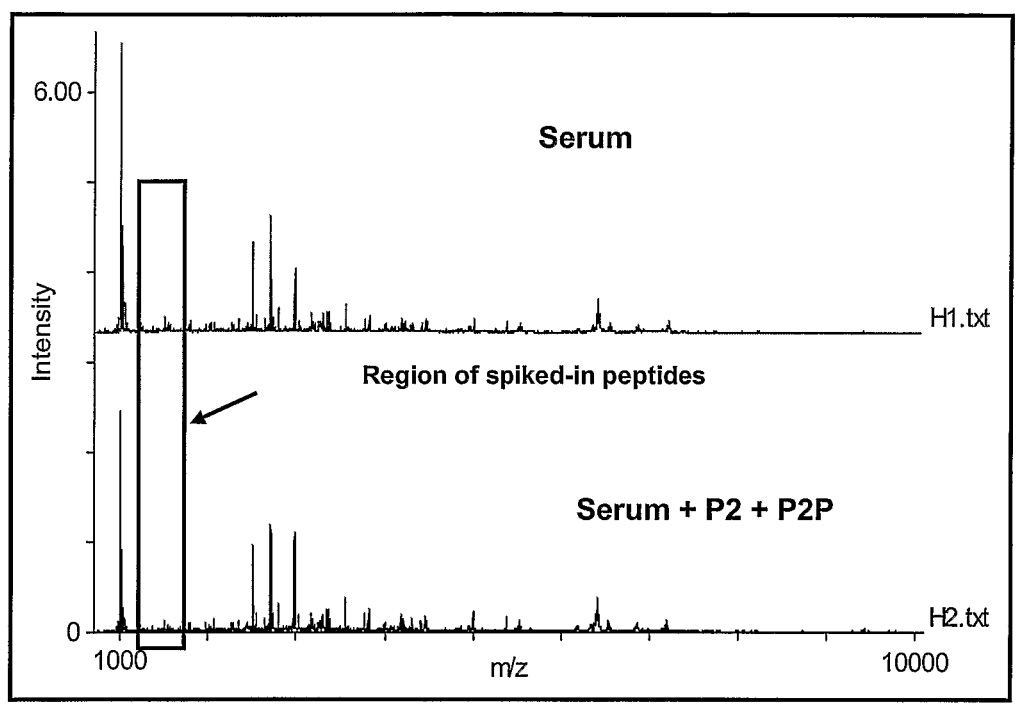
FIG. 12A shows mass spectra of serum and serum spiked with phosphorylated (P2P) and non-phosphorylated (P2) peptides.
Figure 12B:
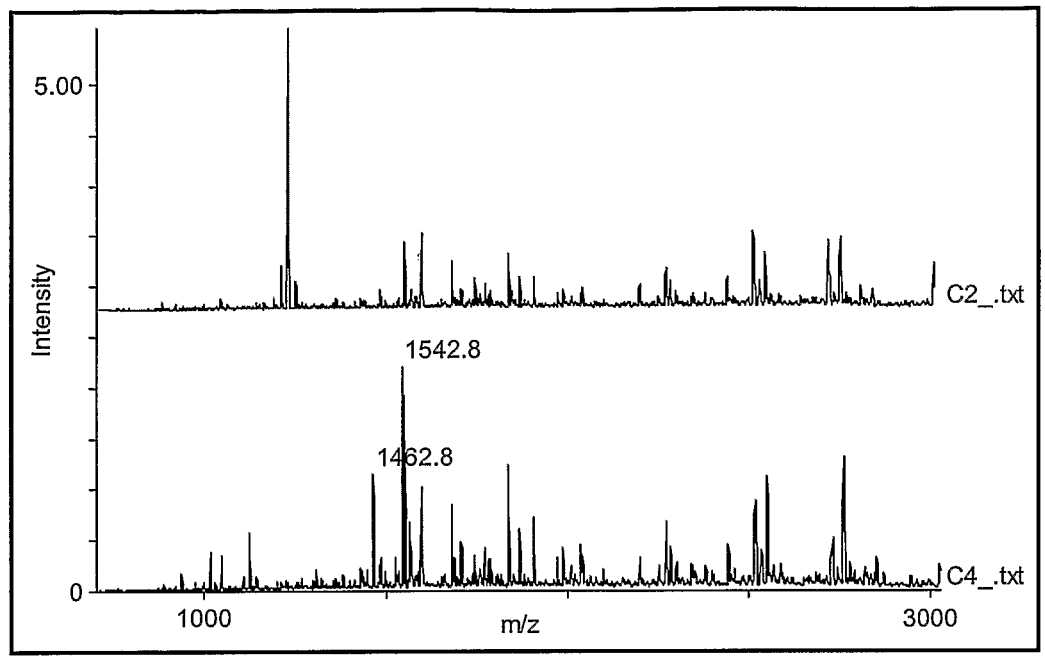
FIG. 12B shows mass spectra of peptides that bound to titanium oxide coated membrane.
Figure 12C:
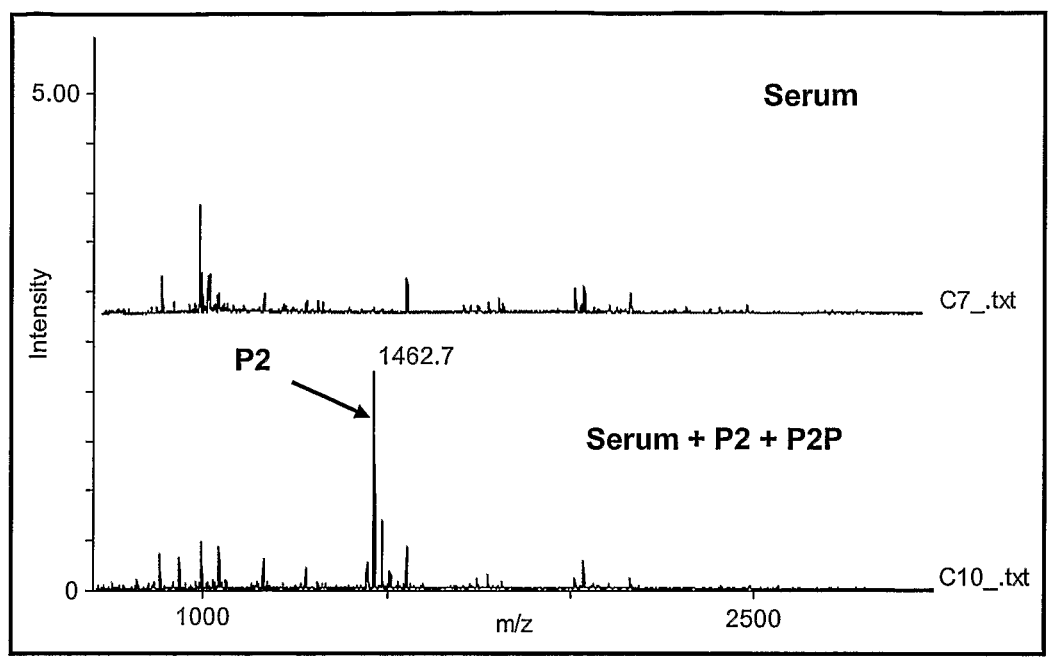
FIG. 12C shows mass spectra of peptides that did not appreciably bind to the membrane (flow-through fraction).

The results are represented in FIG. 12. FIG. 12A shows mass spectra of unspiked serum and serum containing P2 and P2P prior to fractionation. FIG. 12B shows mass spectra of fractions that bound to the phosphoaffinity material. FIG. 12C shows mass spectra actions that did not bind to the phosphoaffinity material. There were no spiked peptides detected in serum samples that had not been fractionated on titanium dioxide particles. Principally non-phosphorylated P2 peptide was detected in the fraction unbound to titanium dioxide from the spiked serum sample. In summary, enrichment of the phosphorylated P2P peptide was observed in the eluted fraction from titanium dioxide particles.

EXAMPLE 7

This example describes isolation of a phosphopeptide from an enzyme digest sample using a titanium dioxide phosphoaffinity material in membrane format.

Phosphopeptides were isolated from a complex peptide mixture generated from trypsin-digested bovine β-casein. About 100 μg of bovine β-casein in 100 mM ammonium carbonate buffer pH 8.5 was digested with 5 μg of trypsin (Sigma) for 16 hours. The enzymatic reaction was stopped by adding formic acid to 3% final concentration. Three samples of casein digest were prepared by diluting 5 μl of the digest sample with the Binding Buffer (see Example 5) by 20-fold. The resulting samples were fractionated on titanium dioxide coated MULTISCREEN membrane plates and analyzed following the procedures described in Example 5. Samples concentrated on ZipPlate without titanium dioxide fractionation and casein digest directly spotted on MALDI Chip were used as controls.

Figure 13:
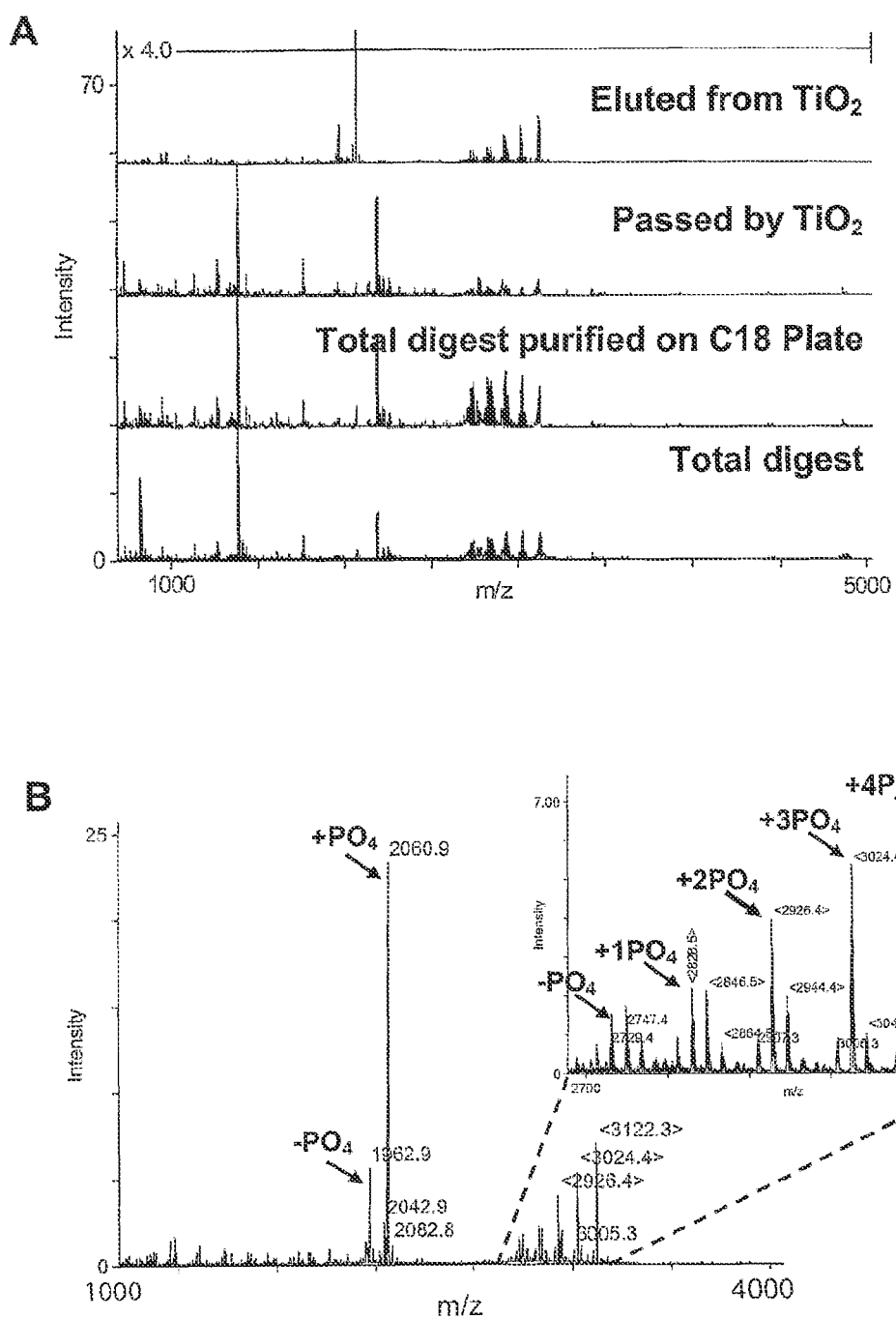
FIG. 13 shows selective isolation of phosphopeptides from trypsin-digested beta casein using a titanium dioxide phosphoaffinity material.

The results are represented in FIG. 13. FIG. 13A shows distribution of peaks in MS spectra of peptides eluted from titanium dioxide, peptides unbound to titanium dioxide, and peptides present in the tryptic digest of β-casein in the range of m/z values from 700 to 5000. FIG. 13B shows a detailed representation of variants of phosphorylated peptides enriched from the trypsin-digested bovine β-casein sample. These results indicate that both monophosphorylated, biphosphorylated, triphosphorylated and tetraphosphorylated peptides were isolated using titanium dioxide coated membranes.

EXAMPLE 8

This example describes isolation of phosphoproteins from a 5-protein mixture using a titanium dioxide phosphoaffinity material in membrane format.

A five protein mixture ($P_{mix}5$) was prepared by combining equal weights of bovine serum albumin (BSA), ovalbumin, carbonic anhydrase, myoglobin, and β-lactoglobulin. Stock solution of $P_{mix}5$ was diluted 1:10 in Binding Buffer (Example 5). One half of the samples were also diluted 1:10 in Binding Buffer containing 1% TRITON X100 to reduce non-specific interactions of proteins with titanium dioxide.

Titanium dioxide isolation of proteins was performed as described above in the previous examples except that three additional stringency washes with 200 μl of 50 mM Tris-Acetate pH 7.5+1% Triton X100 were added to reduce non-specific interactions of proteins with titanium dioxide. Also, an additional elution step was introduced in which the ammonium phosphate buffer used in the initial elution was supplemented with 1% SDS in the second elution. Addition of SDS resulted in more quantitative elution of proteins. Protein samples were precipitated with acetone and analyzed on a 12% Bis-Tris mini-gel (Invitrogen). Gels were stained using SyproRuby total protein gel stain (Molecular Probes). Protein bands were quantified and the enrichment ratios of ovalbumin relative to other non-phosphorylated proteins were calculated.

Figure 14:
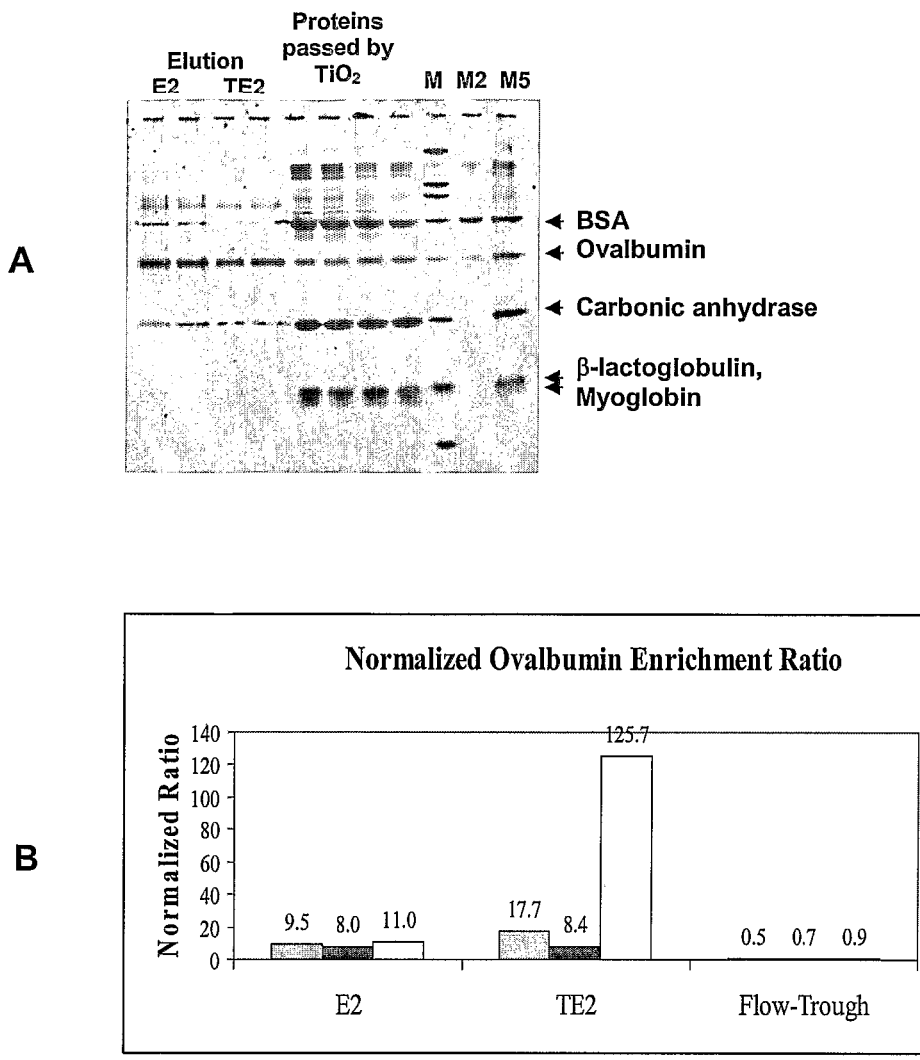
FIG. 14 shows selective isolation of phosphorylated ovalbumin from a five-protein mixture using a titanium dioxide phosphoaffinity material.

FIG. 14 shows results of these experiments. Proteins in the $P_{mix}5$ included phosphorylated ovalbumin (OVA) and 4 non-phosphorylated proteins (bovine serum albumin (BSA), carbonic anhydrase (CAH), myoglobin (Myo), and β-lactoglobulin), as are indicated on the SDS-PAGE gel shown as FIG. 14A. Two types of eluted samples are represented—samples bound to the titanium dioxide membrane in the presence of 1% TRITON X100 (TE2) or without it (E2). Ovalbumin enrichment ratio relative to non-phosphorylated proteins was calculated as a ratio of corresponding band intensities on the gel. Normalized ovalbumin enrichment ratios with respect to BSA, CAH and myo are shown in FIG. 14B. These ratios were normalized to the corresponding ratios in the unfractionated sample (M5). M=Molecular weight markers; M2=BSA+Ovalbumin binary protein mix. These data indicated that at least 8-fold enrichment of phosphorylated ovalbumin was observed using titanium oxide coated membranes. Increased enrichment to about 50-dold (on average with respect to BSA, CAH and myo) was observed when samples were eluted in the presence of detergent.

EXAMPLE 9

This example describes enrichment of phosphomolecules in an array format.

The combination of multi-well microplates and robotic liquid handling instrumentation provides a convenient and powerful technology platform for high-throughput sample processing in drug discovery and lead compound screening. The microplate/liquid handler platform permits large numbers of samples or assays to be processed in a parallel fashion. Polystyrene-based multi-well plates are standard for many applications because the plastic is easy to mold accurately, displays good rigidity for handling by robotic systems, and provides the optical clarity for plate reading. Polypropylene plates are commonly employed in applications involving polymerase chain reaction (PCR) because it has a lower binding capacity for proteins and nucleic acids than polystyrene. Additionally, it can be molded thinly in order to improve heat transfer. Multi-well microplates are available with various functional coatings, such as streptavidin for the capture of biotinylated molecules, as well as with various types of filters incorporated into the base in order to facilitate purification of various molecules of interest.

Microplate-based phosphoprotein purification can be accomplished as follows. A protein sample is obtained from the specimen to be analyzed. Delipidation can be used for enrichment of phosphoproteins from complex specimens, such as cell lysates. Such samples will contain phosphorylated molecules other than phosphoproteins, such as phospholipids, that can adversely impact recovery of phosphoproteins according to the present methods and systems. An example of a successful clean-up method for the preparation of proteins prior to multi-well microplate-based phosphoprotein enrichment is chloroform-methanol precipitation. For example, 600 microliters of methanol is added to 150 microliters (150-300 micrograms) of protein sample and the sample is mixed well using a vortex mixer. Then, 150 microliters of chloroform is added and the sample is once again mixed thoroughly. Next, 450 microliters of deionized water is added and the sample is mixed thoroughly. The specimen is then centrifuged at roughly 12,000 revolutions per minute (rpm) using a tabletop microcentrifuge. The upper phase obtained from the resulting two-phase separation is discarded, while care is taken so that the white precipitate that forms at the interface between the two phases is retained. 450 microliters of methanol is then added, the sample is mixed well and once again centrifuged at 12,000 rpm for five minutes, producing a pellet at the bottom of the tube. The entire supernatant is discarded and the pellet is resuspended in a suitable buffer for the affinity purification procedure, as detailed below. Suitable cocktails of protease and phosphatase inhibitors can be employed to preserve the integrity of the biological sample throughout sample preparation. The described sample cleanup procedure serves only as an example and numerous other methods can be employed (e.g., delipidation can effectively be performed using an ion-exchange pre-purification of sample), with choice of procedure dictated somewhat by the nature of the biological sample under study. Biological fluids, culture media, suspension cell cultures, adherent cell cultures, bacteria, plant tissue and animal tissue can require different sample preparation procedures. For example, solid materials, such as animal tissues, organs or whole organisms, can require additional preparation prior to delipidation, such as mechanical disaggregation using a blender and/or enzymatic disaggregation using collagenase and/or elastase.

Once a suitable sample is prepared, the material is resuspended in an appropriate buffer in order to conduct the affinity fractionation, keeping in mind the isoelectric point of the hydrated metal oxide surface. For titanium oxide-based separation devices, binding buffers with pH values less than 6.0, such as pH values of around 5.0 to 5.5, are suitable for the intended application. An example of a suitable buffer for resuspension of the biological material prior to fractionation on a titanium oxide-based matrix is 0.5 M sodium acetate, 0.2 M sodium chloride, pH 5.5. More acidic buffers of pH 3-4 can induce certain proteins to precipitate from solution, and buffers of even lower pH values can lead to decomposition of certain titanium oxide supports, such as amorphous or microcrystalline layers. Phosphopeptides can be captured by the phosphoaffinity material using more acidic buffers than is optimal for phosphoproteins so long as the hydrated metal oxide matrix is stable under the selected binding conditions. Binding buffers are generally formulated to avoid presence of phosphate or pyrophosphate, since these ions can reduce or even eliminate binding of the phosphorylated molecules to the matrix. Other additives can be included in the binding buffer in order to facilitate solubilization of the proteins. Examples of such additives include Triton X-100, sodium deoxycholate, urea, thiourea and sodium dodecyl sulfate. Sample treatment with nucleases, such as DNAse I or RNAse A, can be useful for cleaving nucleic acids that otherwise can render samples too viscous for optimal filtration. Addition of kinase and or phosphatase inhibitors can also be employed for preserving the phosphorylation status of the biological molecules during isolation.

Enrichment of phosphoproteins or phosphopeptides is achieved using a filtration device, such as a spin column or multi-well microplate, containing a porous or semi-porous hydrated metal oxide surface or coating. First, the filtration device is typically pre-wetted by application of a small amount, about 100 µl, of the binding buffer, though pre-wetting with other media, such as water, or 70% ethanol can be appropriate in certain instances. After about one or more minutes, the buffer can be removed through vacuum filtration, aspiration, centrifugation or other means. Once pre-wetted, the plate can be kept damp before filtering to avoid a need for rewetting. Next, sample prepared in appropriate binding buffer is added to the filtration device and allowed to incubate with the hydrated metal oxide affinity support for a sufficient period of time to permit interaction of the phosphorylated molecules with the hydrated metal oxide surface. The sample is removed through vacuum filtration, aspiration, centrifugation or other means. Then the device is washed with additional binding buffer using the same basic approach. Typically, several volumes of binding buffer are repeatedly applied to remove nonselectively associated sample components, leaving the phosphorylated molecules associated with the phosphoaffinity membrane.

After undesired materials have been removed by application of the wash buffer, the phosphorylated polypeptides can be eluted with an appropriately formulated elution buffer. In an analogous manner as with the binding buffer, choice of the composition of elution buffers can be influenced by biophysical constraints related to the affinity support and by properties of the phosphomolecules. Highly basic elution buffers can reduce stability of the phosphoaffinity material (particularly in cases where the surface is amorphous or microcrystalline) and can cause dephosphorylation of phosphomolecules through alkaline-induced elimination of the phosphate group from phosphoserine and phosphothreonine residues. Under certain circumstances, it can be desirable to dephosphorylate these residues prior to application to the filtration device, in order to selectively detect or isolate proteins containing phosphotyrosine residues. While eluting at pH values higher than the isoelectric point of the hydrated metal oxide is one option for recovering phosphorylated molecules from the matrix, the phosphomolecules can also be competitively eluted from the matrix using phosphate-containing buffers, such as phosphate-buffered saline, pH 7.4. Once eluted, the phosphomolecules can be applied to a desalting device, such as a C-18 reverse-phase packing or an anion-exchange medium, or alternatively can be precipitated with organic solvent, such as ice-cold acetone, or used directly.

EXAMPLE 10

This example describes detection of a phosphorylated polypeptide in sodium dodecyl sulfate (SDS)-polyacrylamide gels.

Described below is an exemplary procedure for detecting a phosphorylated polypeptide, such as a phosphoprotein or phosphopeptide in an SDS-PAGE gel, using a phosphoaffinity material. In this case, the phosphoaffinity material is a hydrated metal oxide such as yttrium oxide, yttrium aluminum garnet or titanium dioxide in particle or crystal form. A protein sample is separated by SDS-polyacrylamide gel electrophoresis according to standard procedures. After electrophoresis, the gel is fixed in an acid- and alcohol-containing solution, such as 50% methanol, 10% acetic acid and is then washed in deionized water to remove the fixative solution. The gel is then added to a solution containing phosphoaffinity particles/crystals and incubated for 2 hours to overnight at room temperature with gentle shaking (i.e. ~50 RPM on an orbital shaker). The solution containing the phosphoaffinity particles can contain simple alcohols, buffer, salts and/or acids in order to facilitate binding of the phosphoaffinity particles with the phosphoproteins and minimize nonselective binding to the gel matrix or other anionic macromolecules within the sample. The gels are washed in a buffer of similar composition as that used during the binding event, except that phosphoaffinity particles are absent from the solution. Alternatively, the gel is incubated in deionized water. The gel is then incubated in a solution that contains a colored or fluorescent dye that selectively binds to the phosphoaffinity particles. The selected dye generally has little or no avidity for the proteins or gel matrix. One fluorescent dye known to bind to silica in diatoms is 2-(4-pyridyl)-5-((4-(2-dimethylaminoethylaminocarbamoyl) methoxy)phenyl)oxazole (PDMPO) and this compound can also interact with other metal oxides to serve as a fluorescent reporter (Shimizu et al, 2001). Typically, sulfonated dyes are avoided as they are bind to proteins, though addition of a small molecule sulfonated compound can minimize this nonspecific interaction. The gel is then incubated again with shaking and excess dye is removed. Phosphorylated polypeptides are detected by visual observation, or by using a device such as a UV-based CCD camera detection system, a laser-based gel scanner, a xenon-arc-based CCD camera detection system, a Polaroid camera combined with a UV-transilluminator or a variety of other devices used for detecting colored or fluorescent moieties. Similar approaches are employed when detecting electrobloted phosphoproteins on polymeric membranes, such as nitrocellulose or polyvinylidene difluoride membranes. Generally, incubation periods are shorter for transfer membranes due to better accessibility of polypeptides to detection reagents.

EXAMPLE 11

This example describes detection of a phosphorylated polypeptide in a matrix using a pre-derivatized polypeptide sample.

Detection of phosphoproteins or phosphopeptides in gels or on blots can be performed using a phosphoaffinity material with samples pre-derivatized with a fluorophore. In this case, the phosphoaffinity material is a hydrated metal oxide such as yttrium oxide, yttrium aluminum garnet or titanium dioxide in particle or crystal form. For labeling of protein samples, succinimidyl esters of the cyanine dyes, Cy2, Cy3 and Cy5, can be employed to fluorescently label as many as three different complex protein populations prior to mixing them together and running them simultaneously on the same 2D gel using a method referred to as difference gel electrophoresis (DIGE) (Unlu et al, 1997). Images of the 2D gels are acquired using as many as three different excitation/emission filters, and the ratio of the differently colored fluorescent signals is used to find protein differences among the samples. DIGE allows two to three samples to be separated under identical electrophoretic conditions, simplifying the process of registering and matching the gel images. One application of this technology is for examining differences between two samples (e.g., drug-treated-vs-control cells or diseased-vs-healthy tissue). Gels or blots can be incubated in phosphoaffinity particles as described above in Example 10. Certain particles can quench the signal from the fluorophore-labeled phosphoproteins and comparison of the fluorescent profiles generated from gels before and after incubation with the particles indicate which proteins in the profile are Phosphorylated by subtractive analysis of the two images generated. A similar approach can be used when the inherent fluorescence of proteins, arising primarily from tryptophan fluorescence, is employed in order to visualize proteins (Roegener et al, 2003).

EXAMPLE 12

This example describes detecting phosphoaffinity materials or phosphomolecule-phosphoaffinity material complexes using inductively-coupled plasma mass spectrometry.

This example describes one type of analytical approach for elemental analysis—inductively-coupled plasma mass spectrometry (ICP-MS). Using ICP-MS, as little as 1 part per billion (ppb) of metal ions can be detected. The ionized conversion of aluminum, which has a first ionization potential of 5.986 electron volts, is 99% under identical run conditions as described for phosphorous in Wilbur and McCurdy, 2001. Thus, following the procedure outlined in Wilbur and McCurdy, 2001 for detecting Al (III) instead of phosphorous improves detection 16-fold. In addition, the specific detection of the metals can move the detection window away from sample background signal.

For the sake of background information, inductively-coupled plasma mass spectrometry (ICP-MS) is useful for trace elemental analysis of environmental, biological, and pharmaceutical samples. Laser ablation ICP-MS permits trace element analysis by combining the spatial resolution of an ultraviolet laser beam with the mass resolution and element sensitivity of a modern ICP-MS. UV laser light, usually produced at a wavelength of 193-266 nm is focused on a sample surface, causing sample ablation. Ablation craters of 15-20 microns are routinely produced by the instrumentation. No special sample preparation is required for the procedure. Ablated material is transported in an argon carrier gas directly to the high temperature inductively-coupled plasma and the resulting ions are then drawn into a mass spectrometer for detection and counting. A mass filter selects particles on the basis of their charge/mass ratio so that only specific isotopes are allowed through the filter and can enter the electron multiplier detector mounted at the end of the mass spectrometer (quadrupole, magnetic sector or time-of-flight instrumentation). Detected signals of individual isotopes can be converted to isotopic ratios or, when standards are measured along with the unknowns, to the actual element concentrations.

ICP-MS-based detection of phosphoaffinity materials or phosphomolecule-phosphoaffinity material complexes can be performed according to the following exemplary procedure. First, phosphorylated molecules are bound to spots of immobilized binding partners (for example, antibodies, aptamers, or any other affinity molecule selective for the molecules) contained on a microarray. Then, the array is incubated with one or more types of phosphoaffinity materials. Next, the array is washed in a buffer, such as 50 mM sodium acetate, pH 6.0, 50 mM magnesium chloride to remove excess phosphoaffinity material. The individual spots on the array are subjected to laser ablation ICP-MS by methods similar to those described, for example, in Marshall et al, 2002 and Wind et al, 2003, except that the relevant metal signal is quantified (rather than the phosphorous signal.) Detection using a laser-ablation ICP-mass spectrometer instrument is generally carried out by directing an ultraviolet laser ablation beam, usually in the form of a collimated beam, toward a focusing lens. The lens can focus the beam to a high flux density on a particular microarray spot, causing local ablation. The ablated molecules are captured in an ICP sampling tube, where they are carried by a flow of carrier gas away from the microarray. The carrier gas is generally provided in a manner that floods the vicinity of the area subject to ablation. The carrier gas and ablated molecules are carried to an ICP-mass spectrometer instrument where the molecules are ionized in the plasma followed by mass identification in the spectrometer.

An exemplary ICP-MS-based detection procedure can involve the following steps. First, phosphomolecules are captured on a microarray containing antibodies, aptamers or other affinity molecules selective towards molecules of interest. Next, the array is incubated with a colloidal solution of hydrated metal oxide particles. Next, the array is washed repeatedly in a buffer, such as 50 mM sodium acetate, pH 6.0, 50 mM magnesium chloride to remove excess colloidal metal particles. The individual spots on the array are subjected to laser ablation ICP-MS by methods similar to those described in Marshall et al, 2002 and Wind et al, 2003, except that the relevant metal signal is quantified rather than the phosphorous signal. Sampling can be performed by single or multi-spot analysis, straight line scans or rastering.

EXAMPLE 13

This example describes an exemplary solid support assay carried out using a phosphoaffinity material incorporating a hydrated metal oxide, in particle form, as a detection agent.

The assay is carried out as follows. Binding partners for phosphorylated molecules are immobilized as spots on the surface of a solid support. The binding partners can be, for example, antibodies, peptides, aptamers, and the like. The spots can contain different binding partners or can be replicate spots. A sample suspected to contain phosphorylated molecules capable of binding to the binding partners is applied to the solid support surface, and the solid support is incubated. As with conventional microarray type support, incubation can be performed in the open, under a coverslip, or in an incubation instrument. After incubation, the sample is washed from the solid support to remove excess and nonselectively bound phosphoaffinity particle and other molecules. Buffers containing inorganic phosphate, such as phosphate-buffered saline, are generally avoided because phosphate can compete for binding of phosphoaffinity particles, and reduce the amount of phosphoaffinity particles bound to phosphorylated molecules.

The spots now contain the binding partners plus whatever complementary proteins have been bound to them during incubation with the sample. A suspension of metal oxide nanoparticles, such as titanium dioxide particles, is then applied to the solid support, allowed to incubate, and the excess is then is washed off. The phosphoaffinity particles bind selectively to the phosphorylated residues in proteins captured on the spots of the solid support.

At this stage, the spots include the binding partners plus the captured complementary proteins with their phosphorylated residues labeled with metal oxide nanoparticles. To enable fluorescent detection of the nanoparticles, a dye solution containing a metal oxide-specific dye, such as rhodamine B or rhodamine 6G, for example, is applied to the solid support and incubated. After incubation, excess and unbound dye is washed off.

Fluorescent detection of the dye is then performed using conventional methods. For example, a beam of excitation light comprising wavelengths overlapping the extinction band of the dye is directed to a beam-splitter element, which directs the excitation beam onto the objective lens. The lens focuses the beam onto a small area of the solid support surface. If dye is present at the focus, it emits fluorescence light at a longer wavelength. A fraction of the emitted fluorescence light is captured by the lens and formed into a beam. The beam-splitter passes the fluorescence light to a detector, such as a photomultiplier tube or CCD array. Typically an emission filter is placed before the detector to block any wavelengths not generated by the dye fluorescence. The fluorescence signal is proportional to the local area concentration of the dye, and hence to the local concentration of phosphorylated residues. In fluorescent detection, a variety of optical detection arrangements can be used in place of the epi-fluorescent shown. The excitation can be evanescent or off-axis dark-field illumination, for example. The emission can be imaged from a line or area of the substrate to a line or area array detector, or can be collected point-by-point with a scanning system and a single-element detector.

Although the invention has been described with reference to the disclosed embodiments, those skilled in the art will readily appreciate that the specific experiments detailed are only illustrative of the invention. It can be understood that various modifications can be made without departing from the spirit of the invention.

The following publications are incorporated herein by reference, in their entireties:

[01] Coletti-Previero M A, Previero A. (1989) Anal Biochem. 180:1-10;
[02] Kawasaki, A., Kobashi, T., and Takahagi, M. (Oct. 7, 2004) United States Application Publication Pub. No. US 2004/0198712 A1, Kuroda I, Shintani Y, Motokawa M, Abe S, Furuno M. (2004) Anal Sci. 20:1313-1319;
[03] Miyazaki S, Morisato K, Ishizuka N, Minakuchi H, Shintani Y, Furuno M, Nakanishi K. (2004) 1043:19-25;
[04] Niesen, T P, De Guire, M R (2001). J. Electroceram. 6: 169-207;
[05] Pinkse M W, Uitto P M, Hilhorst M J, Ooms B, Heck A J. (2004) Anal Chem. 76:3935-3943,
[06] Sano A, Nakamura H. (2004a) Anal Sci. 20:565-566;
[07] Sano A, Nakamura H. (2004b) Anal Sci. 20:861-864;
[08] Zeng L, Li X, Liu J. (2004) Adsorptive removal of phosphate from aqueous solutions using iron oxide tailings. Water Res. 38:1318-1326.
[09] Damen J J, Ten Cate J M, Ellingsen J E. J Dent Res. 1991 October; 70(10):1346-9. Erratum in: J Dent Res 1992 January; 71(1):78;
[10] Debruyne I. Anal Biochem. 1983 August; 133(1):110-5;
[11] Ficarro S B, et al. Nat. Biotechnol. 2002 March; 20(3): 301-5;
[12] Ishikawa F, et al. J AOAC Int. 2003 March-April; 86(2): 215-21;
[13] Kim M S, Chung J G. J Colloid Interface Sci. 2001 Jan. 1; 233(1):31-37;
[14] Koppel R, Litvak M, Solomon B. J Chromatogr B Biomed Appl. 1994 Dec. 9; 662(2):191-6;
[15] Kornblum S S, Lopez B. J Pharm Sci. 1970 July; 59(7): 1016-8;
[16] Lillie R D, et al. Histochemistry. 1976 Oct. 7; 49(1):23-35;
[17] Augugliaro et al. Ann Chim. 2003 July-August; 93(7-8): 639-48;
[18] Grosman J, Vardaxis N J. Biotech Histochem. 1997 November; 72(6):299-303;
[19] Marshall, P. et al. (2002) Analyst 127: 459-461;
[20] Marshall P N, Horobin R W. Histochemie. 1973 Jun. 29; 35(4):361-71;
[21] Steinberg et al. Proteomics. 2003a July; 3(7):1244-55;
[22] Martin K, et al. Comb Chem High Throughput Screen. 2003b June; 6(4):331-9;
[23] Meloan S N et al. Beitr Pathol. 1973 September; 149(4): 386-95;
[24] Mustafa S, et al. Environ Technol. 2004 January; 25(1): 1-6;
[25] Posewitz M C, Tempst P. Anal Chem. 1999 Jul. 15; 71(14):2883-92;
[26] Pugniere M, et al. Biosci Rep. 1988 June; 8 (3):263-9;
[27] Quinn R C, Zent A P. Orig Life Evol Biosph. 1999 January; 29(1):59-72;
[28] Roegener J, et al. Anal Chem. 75(1):157-9;
[29] Sano A, Nakamura H. Anal Sci. 2004a March; 20(3): 565-6;
[30] Sano A, Nakamura H. Anal Sci. 2004b May; 20(5):861-4;
[31] Saquib M, Muneer M. J Environ Sci Health Part A Tox Hazard Subst Environ Eng. 2003; 38(11):2581-98;
[32] Schulenberg B, et al. J Biol. Chem. 2003 Jul. 18; 278 (29):27251-5;
[33] Steinberg T H, et al. Proteomics. 2003 July; 3(7):1128-44;
[34] Shimizu K, et al. Chem. Biol. 2001 November; 8(11): 1051-60;

[35] Vogel R, et al. Spectrochim Acta A Mol Biomol Spectrosc. 2004 January; 60(1-2):245-9;
[36] Unlu M, et al. Electrophoresis. 1997 October; 18(11): 2071-7;
[37] Wang L, et al. Spectrochim Acta A Mol Biomol Spectrosc. 2004 March; 60(4):747-50;
[38] Wilbur, S, and McCurdy, E. (2001) "Electrophoresis 24: 1276-1280;
[39] Marshall P N, Horobin R W. Agilent Document 5988-4286EN;
[40] Wind, M., et al. (2003) Electrophoresis 24: 1276-1280;
[41] Marshall P N, Horobin R W Electrophoresis 24: 1276-1280;
[42] Wang S, et al. Spectrochim Acta A Mol Biomol Spectrosc. 2003 April; 59 (6): 1139-44;
[43] Wou L L, Mulley B A. J Pharm Sci. 1988 October; 77(10):866-71;
[44] Yezek L, et al. J Colloid Interface Sci. 2000 May 1; 225(1):227-232;
[45] Yguerabide J, Yguerabide E E. J Cell Biochem Suppl. 2001; Suppl 37:71-81;
[46] Zeng L, et al. Water Res. 2004 March; 38(5):1318-26.

What is claimed is:

1. A method for detecting a phosphomacromolecule in a sample comprising:
   (a) contacting the sample with a phosphoaffinity material comprising titanium dioxide, under conditions wherein the phosphomacromolecule is capable of binding to the phosphoaffinity material to form a phosphomacromolecule-phosphoaffinity material complex, wherein the phosphoaffinity material further comprises a support and wherein the support is selected from the group consisting of a particle, bead, gel, matrix, membrane, filter, fiber, sheet, mesh, frit, resin, sample vessel, column, pipette tip, slide channel, and MALDI-TOF plate; and
   (b) detecting formation of the phosphomacromolecule-phosphoaffinity material complex, thereby detecting the phosphomacromolecule in the sample.

2. The method of claim 1, wherein the detecting comprises measuring binding between the phosphomacromolecule and the phosphoaffinity material.

3. The method of claim 2, wherein the measuring comprises measuring a physiochemical property of the phosphomacromolecule, the phosphoaffinity material, or both, wherein the physiochemical property is selected from the group consisting of absorbance, transmission, mass measurement, fluorescence intensity, fluorescence polarization, fluorescence resonance energy transfer, time-resolved fluorescence, resonance light scattering, surface-enhanced Raman scattering, electron paramagnetic resonance, refractive index absorbance, nuclear magnetic resonance, surface Plasmon resonance, refractive index changes, and combinations thereof.

4. The method of claim 1, wherein the detecting comprises detecting the phosphoaffinity material portion of the phosphomacromolecule-phosphoaffinity material complex.

5. The method of claim 4, wherein the titanium dioxide of the phosphoaffinity material portion is detected.

6. The method of claim 5, wherein the titanium dioxide is detected using mass spectrometry.

7. The method of claim 6, wherein the mass spectrometry is inductively-coupled plasma mass spectrometry.

8. The method of claim 1, further comprising labeling the phosphoaffinity material with a detectable tag prior to detecting.

9. The method of claim 8, wherein the detectable tag is a fluorescent moiety.

10. The method of claim 1, wherein the titanium dioxide is labeled with a fluorescent moiety.

11. The method of claim 1, wherein the detecting comprises detecting the phosphomacromolecule portion of the phosphomacromolecule-phosphoaffinity material complex.

12. The method of claim 11, wherein the phosphomacromolecule portion is detected by inductively-coupled plasma mass spectrometry.

13. The method of claim 1, wherein the detecting comprises detecting fluorescence resonance energy transfer.

14. The method of claim 13, wherein fluorescence resonance energy transfer occurs between a fluorescent tag on the phosphomacromolecule and a fluorescent tag on the phosphoaffinity material.

15. The method of claim 1, wherein the titanium dioxide is in particle form.

16. The method of claim 1, wherein the support comprises an inorganic material.

17. The method of claim 1, wherein the support is a particle.

18. The method of claim 17, wherein the particle comprises a colloidal metal.

19. The method of claim 1, wherein the support comprises an organic material.

20. The method of claim 1, wherein the support is a sheet.

21. The method of claim 20, wherein the sheet comprises cellulose.

22. The method of claim 1, wherein the support comprises a detectable tag.

23. The method of claim 1, wherein the phosphomacromolecule is a phosphorylated polypeptide.

24. The method of claim 1, wherein the sample comprises a support.

25. The method of claim 1, wherein the sample comprises a detectable tag.

26. The method of claim 1, further comprising:
   (c) isolating the phosphomacromolecule-phosphoaffinity material complex from the sample, thereby isolating the phosphomacromolecule from the sample.

27. The method of claim 26, further comprising separating the phosphomacromolecule from the phosphomacromolecule-phosphoaffinity material complex.

28. The method of claim 1, wherein the phosphomacromolecule is a phosphorylated polynucleotide.

29. The method of claim 1, wherein the phosphomacromolecule is a phosphorylated lipid.

30. The method of claim 1, wherein the phosphomacromolecule is a phosphorylated carbohydrate.

31. The method of claim 1, wherein the support is a magnetic particle.

32. The method of claim 1, wherein the support is a bead.

33. The method of claim 1, wherein the support is a magnetic bead.

* * * * *